US011998586B2

(12) United States Patent
Urish et al.

(10) Patent No.: US 11,998,586 B2
(45) Date of Patent: Jun. 4, 2024

(54) COMPOSITIONS COMPRISING ANTIMICROBIAL PEPTIDES

(71) Applicant: University of Pittsburgh—Of the Commonwealth System of Higher Education, Pittsburgh, PA (US)

(72) Inventors: Kenneth Urish, Sewickley, PA (US); Jonathan Brendan Mandell, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/525,344

(22) Filed: Nov. 12, 2021

(65) Prior Publication Data

US 2022/0054589 A1 Feb. 24, 2022

Related U.S. Application Data

(63) Continuation of application No. PCT/US2020/059415, filed on Nov. 6, 2020.

(60) Provisional application No. 63/028,636, filed on May 22, 2020, provisional application No. 62/932,609, filed on Nov. 8, 2019.

(51) Int. Cl.
*A61K 38/00* (2006.01)
*A61K 31/546* (2006.01)
*A61K 38/10* (2006.01)
*A61K 38/17* (2006.01)

(52) U.S. Cl.
CPC ............ *A61K 38/10* (2013.01); *A61K 31/546* (2013.01); *A61K 38/1729* (2013.01)

(58) Field of Classification Search
CPC ... A61K 38/10; A61K 31/546; A61K 38/1729
See application file for complete search history.

(56) References Cited

U.S. PATENT DOCUMENTS

| | | | |
|---|---|---|---|
| 5,504,190 A | 4/1996 | Houghten et al. | |
| 5,714,577 A | 2/1998 | Montelaro et al. | |
| 5,981,698 A | 11/1999 | Brittain | |
| 6,835,713 B2 | 12/2004 | Montelaro et al. | |
| 6,887,847 B2 | 5/2005 | Montelaro et al. | |
| 8,071,540 B2 | 12/2011 | Montelaro et al. | |
| 2003/0036627 A1 | 2/2003 | Montelaro et al. | |
| 2004/0043041 A1 | 3/2004 | Baker, Jr. et al. | |
| 2005/0025761 A1 | 2/2005 | Thorpe et al. | |
| 2005/0282239 A1 | 12/2005 | Allbritton et al. | |
| 2007/0225213 A1 | 9/2007 | Kosak | |
| 2009/0053278 A1 | 2/2009 | Fatora et al. | |
| 2009/0099533 A1* | 4/2009 | Montelaro ............... A61L 27/34 623/18.11 |
| 2009/0198200 A1* | 8/2009 | Tumey .................. A61M 1/915 604/305 |
| 2010/0210506 A1* | 8/2010 | Quay ........................ A61P 3/10 514/1.1 |
| 2013/0261534 A1* | 10/2013 | Niezgoda ................ A61M 1/95 604/22 |
| 2015/0118183 A1* | 4/2015 | Baumhof ............. A61K 47/646 424/277.1 |
| 2020/0071361 A1 | 3/2020 | Steckbeck | |
| 2020/0277334 A1 | 9/2020 | Steckbeck | |
| 2022/0249599 A1* | 8/2022 | Steckbeck ............. A61K 38/08 |

FOREIGN PATENT DOCUMENTS

| | | |
|---|---|---|
| EP | 0273716 B1 | 6/1988 |
| WO | 03103718 A2 | 12/2003 |
| WO | 2008070083 A2 | 6/2008 |
| WO | 2018160997 A1 | 9/2018 |
| WO | 20181876617 A1 | 10/2018 |
| WO | 2019178274 A1 | 9/2019 |
| WO | WO-2021130390 A1 * | 7/2021 |

OTHER PUBLICATIONS

Swedan et al in "Synergism of cationic antimicrobial peptide WLBU2 with antibacterial agents against biofilms of multi-drug resistant Acinetobacter baumannii and Klebsiella pneumoniae" (Infection and Drug Resistance 2019: vol. 12, pp. 2019-2030). (Year: 2019).*

Mandell et al in "Elimination of Antibiotic Resistant Surgical Implant Biofilms Using an Engineered Cationic Amphipathic Peptide WLBU2" (Scientific Reports, 2017 vol. 7: 18098, published online Dec. 22, 2017; pp. 1-9). (Year: 2017).*

Gagne ("Biochemical Ecotoxicology, 2014: Section 2.1.6 Osmolarity"). (Year: 2014).*

Mandell et al "Direct antimicrobial activity of cationic amphipathic peptide WLBU2 against Staphylococcus aureus biofilms is enhanced in physiologic buffered saline" (J Orthop Res. Dec. 2020; vol. 38, No. 12: pp. 2657-2663; Epub Jun. 9, 2020). (Year: 2020).*

Novak et al in "Efficacy of the De Novo-Derived Antimicrobial Peptide WLBU2 against Oral Bacterial" (Antimicrobial Agents And Chemotherapy, May 2007, vol. 51, No. 5: pp. 1837-1839). (Year: 2007).*

Abdelbaqi et al., "Novel engineered cationic antimicrobial peptides display broad-spectrum activity against Francisella tularensis, Yersinia pestis and Burkholderia pseudomallei", Journal of Medical Microbiology, 2016, pp. 188-194, vol. 65.

Arroyo et al., "Membrane Permeabilization by Different Regions of the Human Immunodeficiency Virus Type 1 Transmembrane Glycoprotein gp41", Journal of Virology, Jul. 1995, pp. 4095-4102, vol. 69:7.

Beary et al., "Interruption of T-cell signal transduction by lentivirus lytic peptides from HIV-1 transmembrane protein", Journal of Peptide Research, 1998, pp. 75-79.

(Continued)

*Primary Examiner* — Catherine S Hibbert
(74) *Attorney, Agent, or Firm* — The Webb Law Firm

(57) ABSTRACT

A method of treating or preventing a microbial infection in a patient is provided, along with a wound irrigation system and a composition in the form of an irrigation liquid for reducing microbial load or preventing microbial infection in a wound.

66 Claims, 9 Drawing Sheets

Specification includes a Sequence Listing.

(56) References Cited

OTHER PUBLICATIONS

Beumer et al., "Mass Balance Study of the Engineered Cationic Antimicrobial Peptide, WLBU2, Following a Single Intravenous Dose of 14C-WLBU2 in Mice", Current Review in Clinical and Experimental Pharmacology, 2021, pp. 263-272, vol. 16:3.
Blondelle et al., "Design of Model Amphipathic Peptides Having Potent Antimicrobial Activities", Biochemistry, 1992, pp. 12688-12694, vol. 31:50.
Brown et al., "Dilute Betadine Lavage Before Closure for the Prevention of Acute Postoperative Deep Periprosthetic Joint Infection", The Journal of Arthroplasty, 2012, pp. 27-30, vol. 27:1.
Brutlag et al., "Improved sensitivity of biological sequence database searches", Cabios, 1990, pp. 237-245, vol. 6:3.
Bucki et al., "Resistance of the antibacterial agent ceragenin CSA-13 to inactivation by DNA or F-actin and its activity in cystic fibrosis sputum", Journal of Antimicrobial Chemotherapy, Oct. 2007, pp. 1-12.
Bucki et al., "Salivary mucins inhibit antibacterial activity of the cathelicidin-derived LL-37 peptide but not the cationic steroid CSA-13", Journal of Antimicrobial Chemotherapy, May 2008, pp. 329-335.
Burton et al., "Antibiofilm Activity of GlmU Enzyme Inhibitors against Catheter-Associated Uropathogens", Antimicrobial Agents and Chemotherapy, 2006, pp. 1835-1840, vol. 50:5.
Byfield et al., "Cathelicidin LL-37 Increases Lung Epithelial Cell Stiffness, Decreases Transepithelial Permeability, and Prevents Epithelial Invasion by Pseudomonas aeruginosa", The Journal of Immunology, 2011, pp. 6402-6409.
Caron et al., "Intracellular Delivery of a Tat-eGFP Fusion Protein into Muscle Cells", Molecular Therapy, Mar. 2001, pp. 310-318, vol. 3:3.
Chan et al., "Selective Permeabilization of Gram-Negative Bacterial Membranes Using Multivalent Peptide Constructs for Antibiotic Sensitization", Infectious Diseases, 2021, pp. 721-732, vol. 7.
Chen et al., "Enhanced efficacy of the engineered antimicrobial peptide WLBU2 via direct airway delivery in a murine model of Pseudomonas aeruginosa pneumonia", Clinical Microbiology and Infection, 2018, pp. 1-8, vol. 547.
Chernomordik et al., "An Amphipathic Peptide from the C-Terminal Region of the Human Immunodeficiency Virus Envelope Glycoprotein Causes Pore Formation in Membranes", Journal of Virology, Nov. 1994, pp. 7115-7123, vol. 68:11.
Chou et al., "Prediction of Protein Conformation", Biochemistry, 1974, pp. 22-245, vol. 13:2.
Chou et al., "Prediction of the Secondary Structure of Proteins from their Amino Acid Sequence", U.S. Public Health, pp. 45-148.
Cirioni et al., "Pre-treatment of central venous catheters with the cathelicidin BMAP-28 enhances the efficacy of antistaphylococcal agents in the treatment of experimental catheter-related infection", Peptides, 2006, pp. 2104-2110, vol. 27.
Comardelle et al., "A Synthetic Peptide Corresponding to the Carboxy Terminus of Human Immunodeficiency Virus Type 1 Transmembrane Glycoprotein Induces Alterations in the Ionic Permeability of Xenopus laevis Oocytes", AIDS Research and Human Retroviruses, 1997, pp. 1525-1532, vol. 13:17.
Deslouches et al., "De Novo Generation of Cationic Antimicrobial Peptides: Influence of Length and Tryptophan Substitution on Antimicrobial Activity", Antimicrobial Agents and Chemotherapy, Jan. 2005, pp. 316-322, vol. 49:1.
Deslouches et al., "Activity of the De Novo Engineered Antimicrobial Peptide WLBU2 against Pseudomonas aeruginosa in Human Serum and Whole Blood: Implications for Systemic Applications", Antimicrobial Agents and Chemotherapy, Aug. 2005, pp. 3208-3216.
Deslouches et al., "De novo-derived cationic antimicrobial peptide activity in a murine model of Pseudomonas aeruginosa bacteraemia", Journal of Antimicrobial Chemotherapy, 2007, pp. 669-672, vol. 60.
Deslouches et al., "Rational Design of Engineered Cationic Antimicrobial Peptides Consisting Exclusively of Arginine and Tryptophan, and Their Activity against Multidrug-Resistant Pathogens", Antimicrobial Agents and Chemotherapy, Jun. 2013, pp. 2511-2521, vol. 57:6.
Deslouches et al., "Engineered Cationic Antimicrobial Peptides To Overcome Multidrug Resistance by ESKAPE Pathogens", Antimicrobial Agents and Chemotherapy, Feb. 2015, pp. 1329-1333, vol. 59:2.
Deslouches et al., "Comparative functional properties of engineered cationic antimicrobial peptides consisting exclusively of tryptophan and either lysine or arginine", Journal of Medical Microbiology, 2016, pp. 554-565, vol. 65.
Di et al., "Enhanced therapeutic index of an antimicrobial peptide in mice by increasing safety and activity against multidrug-resistant bacteria", Science Advances, May 2020, pp. 1-10, vol. 6.
Dietz et al., "Delivery of bioactive molecules into the cell: the Trojan horse approach", Molecular and Cellular Neuroscience, 2004, pp. 85-131, vol. 27.
Donlan et al., "Biofilms: Survival Mechanisms of Clinically Relevant Microorganisms", Clinical Microbiology Reviews, Apr. 2002, pp. 167-193, vol. 15:2.
Eisenberg et al., "The hydrophobic moment detects periodicity in protein hydrophobicity", Biophysics, Jan. 1984, pp. 140-144, vol. 81.
Eisenberg et al., "Analysis of Membrane and Surface Protein Sequences with the Hydrophobic Moment Plot", Journal of Molecular Biology, 1984, pp. 125-142, vol. 179.
Eisenberg et al., "The Most Highly Amphiphilic a-Helices Include Two Amino Acid Segments in Human Immunodeficiency Virus Glycoprotein 41", Biopolymers, 1990, pp. 171-177, vol. 29.
El-Ghannam et al., "Nanoporous Delivery System to Treat Osteomyelitis and Regenerate Bone: Gentamicin Release Kinetics and Bactericidal Effect", Jan. 2005, pp. 277-284.
Ellman, "Tissue Sulfhydryl Groups", Archives of Biochemistry and Biophysics, 1959, pp. 70-77, vol. 82.
Falagas et al., "Rifampicin-impregnated central venous catheters: a meta-analysis of randomized controlled trials", Journal of Antimicrobial Chemotherapy, Jan. 2007, pp. 359-369, vol. 59.
File, "Overview of Resistance in the 1990s", Emerging Resistance and Therapeutic Options, 1999, pp. 3S-8S, vol. 115.
Fontenot et al., "A Survey of Potential Problems and Quality Control in Peptide Synthesis by the Fluorenylmethoxycarbonyl Procedure", Peptide Research, 1991, pp. 19-25, vol. 4:1.
Friedrich et al., "Salt-Resistant Alpha-Helical Cationic Antimicrobial Peptides", Antimicrobial Agents and Chemotherapy, Jul. 1999, pp. 1542-1548, vol. 43:7.
Frisch et al., "Intraoperative chlorhexidine irrigation to prevent infection in total hip and knee arthroplasty", Arthroplasty Today, 2017, pp. 294-297, vol. 3.
Fujii et al., "A molecular model for membrane fusion based on solution studies of an amphiphilic peptide from HIV gp41", Protein Science, 1992, pp. 1454-1464, vol. 1.
Ganz et al., "Antimicrobial peptides of leukocytes", Leukocytes, 1997, pp. 53-68.
Garnier et al., "Analysis of the Accuracy and Implications of Simple Methods for Predicting the Secondary Structure of Globular Proteins", Journal of Molecular Biology, 1978, pp. 97-120, vol. 120.
Gawrisch et al., "Interaction of Peptide Fragment 828-242 of the Envelope Glycoprotein of Human Immunodeficiency Virus Type I with Lipid Bilayers", Biochemistry, 1993, pp. 3112-3118, vol. 32.
George et al., "Use of Chlorhexidine Preparations in Total Joint Arthroplasty", Journal of Bone and Joint Infection, 2017, pp. 15-22, vol. 2:1.
Guelen et al., "TAT-apoptin is efficiently delivered and induces apoptosis in cancer cells", Oncogene, 2004, pp. 1153-1165, vol. 23.
Habermann, "Bee and Wasp Venoms", Science, Jul. 1972, pp. 314-322, vol. 177:4046.
Hancock, "Host Defence (Cationic) Peptides What Is Their Future Clinical Potential?", Drugs, Apr. 1999, pp. 469-473, vol. 57:4.

(56) References Cited

OTHER PUBLICATIONS

Heinrich et al., "Synergistic Biophysical Techniques Reveal Structural Mechanisms of Engineered Cationic Antimicrobial Peptides in Lipid Model Membranes", Chemistry, May 2020, pp. 6247-6256, vol. 26:28.
Honig, "Protein Folding: From the Levinthal Paradox to Structure Prediction", Journal of Molecular Biology, 1999, pp. 283-293, vol. 293.
Hwang et al., "Structure-function relationships of antimicrobial peptides", Biochemical Cell Biology, 1998, pp. 235-246, vol. 76.
Isaacs et al., "Inactivation of Herpes Simplex Virus Clinical Isolates by Using a Combination Microbicide", Antimicrobial Agents and Chemotherapy, Mar. 2006, pp. 1063-1066, vol. 50:3.
Tande et al., "Prosthetic Joint Infection", Clinical Microbiology Reviews, Apr. 2014, pp. 302-345, vol. 27:2.
Tande et al., "Clinical Presentation, Risk Factors, and Outcomes of Hematogenous Prosthetic Joint Infection in Patients with *Staphylococcus aureus* Bacteremia", The American Journal of Medicine, 2016, pp. 1-10, vol. 129:2.
Tencza et al., "Effect of Amino Acid Substitutions on Calmodulin Binding and Cytolytic Properties of the LLP-1 Peptide Segment of Human Immunodeficiency Virus Type 1 Transmembrane Protein", Journal of Virology, Aug. 1995, pp. 5199-5202, vol. 69:8.
Tencza et al., "Calmodulin-Binding Function of LLP Segments from the HIV Type 1 Transmembrane Protein Is Conserved among Natural Sequence Variants", AIDS Research and Human Retroviruses, 1997, pp. 263-269, vol. 13:3.
Tencza et al., "Novel Antimicrobial Peptides Derived from Human Immunodeficiency Virus Type 1 and Other Lentivirus Transmembrane Proteins", Antimicrobial Agents and Chemotherapy, Nov. 1997, pp. 2394-2398, vol. 41:11.
Tencza et al., "Lentivirus-derived antimicrobial peptides: increased potency by sequence engineering and dimerization", Journal of Antimicrobial Chemotherapy, 1999, pp. 33-41, vol. 44.
Urish et al., "Antibiotic-tolerant *Staphylococcus aureus* Biofilm Persists on Arthroplasty Materials", Symposium: Proceedings of the 2015 Musculoskeletal Infection Society, Jul. 2016, pp. 1649-1656, vol. 474:7.
Venable et al., "Theoretically Determined Three-Dimensional Structures for Amphipathic Segments of the HIV-1 gp41 Envelope Protein", AIDS Research and Human Retroviruses, pp. 7-22, vol. 5:1.
Von Eiff et al., "Infections Associate with Medical Devices", Drugs, 2005, pp. 180-214, vol. 65:2.
Wachinger et al., "Influence of amphipathic peptides of the HIV-1 production in persistently infected T lymphoma cells", Federation of European Biochemical Societies, 1992, pp. 235-241, vol. 309:3.
Wachinger et al., "Antimicrobial peptides melittin and cecropin inhibit replication of human immunodeficiency virus 1 by suppressing viral gene expression", Journal of General Virology, 1998, pp. 731-740, vol. 79.
Walkenhorst et al., "pH Dependence of Microbe Sterilization by Cationic Antimicrobial Peptides", Antimicrobial Agents and Chemotherapy, 2013, pp. 3312-3320, vol. 57:7.
Ward et al., "Inhibition of protein kinase C by a synthetic peptide corresponding to cytoplasmic domain residues 828-848 of the human immunodeficiency virus type 1 envelope glycoprotein", Cancer Letters, 1995, pp. 37-40, vol. 88.
Wheeler et al., "Intracellular delivery of HSP70 using HIV-1 Tat protein transduction domain", Biochemical and Biophysical Research Communications, 2003, pp. 54-59, vol. 301.
Wild et al., "A synthetic peptide inhibitor of human immunodeficiency virus replication: Correlation between solution structure and viral inhibition", The Proceedings of the National Academy of Sciences, 1992, pp. 10537-10541, vol. 89.
Wu et al., "Adsorption, structural alteration and elution of peptides at pendant PEO layers", Colloids and Surfaces B: Biointerfaces, 2013, pp. 1-18, vol. 112.

Wu et al., "Concentration effects on peptide elution from pendant PEO layers", Colloids and Surfaces B: Biointerfaces, 2014, pp. 210-217, vol. 118.
Wu et al., "Sequential and competitive adsorption of peptides at pendant PEO layers", Colloids and Surfaces B: Biointerfaces, 2015, pp. 69-76, vol. 130.
Yang et al., "Antimicrobial peptide-modified liposomes for bacteria targeted delivery of temoporfin in photodynamic antimicrobial chemotherapy", Photochemistry Photobiology Science, 2011, pp. 1593-1601, vol. 10.
Yasin et al., "Evaluation of the Inactivation of Infectious Herpes Simplex Virus by Host-Defense Peptides", European Journal of Clinical Microbiology & Infectious Diseases, 2000, pp. 187-194, vol. 19.
Yuan et al., "Characterization of the Calmodulin Binding Domain of SIV Transmembrane Glycoprotein by NMR and CD Spectroscopy", Biochemistry, 1995, pp. 10690-10696, vol. 34:33.
Zabner et al., "Adenovirus-Mediated Gene Transfer to Ciliated Airway Epithelia Requires Prolonged Incubation Time", Journal of Virology, 1996, pp. 6994-7003, vol. 70:10.
Zanetti et al., "Cathelicidins: a novel protein family with a common proregion and a variable C-terminal antimicrobial domain", Federation of European Biochemical Societies Letters, 1995, pp. 1-5, vol. 374.
Zhang et al., "Amphipathic domains in the C terminus of the transmembrane protein (gp41) permeabilize HIV-1 virions: A molecular mechanism underlying natural endogenous reverse transcription", Proceedings of the National Academy of Sciences of the United States, 1996, pp. 12519-12524, vol. 93.
Zhang et al., "Interactions of Bacterial Cationic Peptide Antibiotics with Outer and Cytoplasmic Membranes of Pseudomonas Aeruginosa", Antimicrobial Agents and Chemotherapy, 2000, pp. 3317-3321, vol. 44:12.
Zhibao et al., "Characterization of Class Cationic Peptides Able to Facilitate Efficient Protein Transduction in Vitro and In Vivo", Molecular Therapy, 2000, pp. 339-347, vol. 2:4.
Ziegler et al., "The Cationic Cell-Penetrating Peptide CPP Derived from the HIV-1 Protein TAT is Rapidly Transported into Living Fibroblasts: Optical, Biophysical, and Metabolic Evidence", Biochemistry, 2004, pp. 138-148, vol. 44:1.
Zimmerli et al., "Prosthetic-Joint Infections", The New England Journal of Medicine, 2004, pp. 1645-1654, vol. 351:16.
Zmistowski et al., "Periprosthetic joint infection increases the risk of one-year mortality", The Journal of Bone and Joint Surgery Incorporated, 2013, pp. 2176-2184.
Kalia et al., "Rational Site-Directed Mutations of the LLP-1 and LLP-2 Lentivirus Lytic Peptide Domains in the Intracytoplasmic Tail of Human Immunodeficiency Virus Type 1 gp41 Indicate Common Functions in Cell-Cell Fusion but Distinct Roles in Virion Envelope Incorporation", Journal of Virology, Mar. 2003, pp. 3634-3646, vol. 77:6.
Klevens et al., "Estimating Health Care-Associated Infections and Deaths in U.S. Hospitals" Public Health Reports, 2007, pp. 160-166, vol. 122.
Koenig et al., "Effect of the conformation of a peptide from gp41 on binding and domain formation in model membranes", Molecular Membrane Biology, 1995, pp. 77-82, vol. 12.
Kumagai et al., "Elastic behavior of model membranes with antimicrobial peptides depends on lipid specificity and D-enantiomers", Soft Matter, Sep. 2020, pp. 1860-1868, vol. 15:8.
Labruere et al., "Anti-Methicillin-Resistant *Staphylococcus aureus* Nanoantibiotics", Frontiers in Pharmacology, Oct. 2019, pp. 1-24, vol. 10.
Lampi et al., "Structural attributes affecting peptide entrapment in PEO brush layers", Colloids Surface B Biointerfaces, Jun. 2013, pp. 79-85, vol. 106.
Lashua et al., "Engineered cationic antimicrobial peptide (eCAP) prevents Pseudomonas aeruginosa biofilm growth on airway epithelial cells", Journal of Antimicrobial Chemotherapy, May 2016, pp. 2200-2207, vol. 71.

(56) References Cited

OTHER PUBLICATIONS

Lehrer et al., "Antibacterial Activity of Microbicidal Cationic Proteins 1 and 2, Natural Peptide Antibiotics of Rabbit ung Macrophages", Infection and Immunity, Oct. 1983, pp. 10-14, vol. 42:1.
Leszczynska et al., "Bactericidal activities of the cationic steroid CSA-13 and the cathelicidin peptide LL-37 against Helicobacter pylori in simulated gastric juice", BMC Microbiology, 2009, pp. 1-10, vol. 9:187.
Li et al., "Antibiofilm peptides as a promising strategy: comparative research", Applied Microbial and Cell Physiology, 2021, pp. 1647-1656, vol. 105.
Lin et al., "Prevention of ESKAPE pathogen biofilm formation by antimicrobial peptides WLBU2 and LL37", International Journal of Antimicrobial Agents, Nov. 2019, pp. 667-672, vol. 52:5.
Mai et al., "Efficiency of Protein Transduction Is Cell Type-dependent and Is Enhanced by Dextran Sulfate", The Journal of Biological Chemistry, 2002, pp. 30208-30218, vol. 277:33.
Malik et al., "pH Dependent Antimicrobial Peptides and Proteins, Their Mechanisms of Action and Potential as Therapeutic Agents", Pharmaceuticals, 2016, pp. 1-35, vol. 9:67.
Mandell et al., "Elimination of Antibiotic Resistant Surgical Implant Biofilms Using an Engineered Cationic Amphipathic Peptide WLBU2", Scientific Reports, 2017, pp. 1-9, vol. 7:18098.
Mandell et al., "Direct antimicrobial activity of cationic amphipathic peptide WLBU2 against Staphylococcus aureus piofilms is enhanced in physiologic buffered saline", Journal of Orthopedic Research, Dec. 2020, pp. 2657-2663, vol. 38:12.
Mcclanahan et al., "Bioactivity of WLBU2 peptide antibiotic in combination with bioerodible polymer", International Journal of Antimicrobial Agents, Dec. 2011, pp. 530-533, vol. 38:6.
Melvin et al., "Simultaneous Antibiofilm and Antiviral Activities of an Engineered Antimicrobial Peptide during Virus-Bacterium Coinfection", Host-Microbe Biology, 2016, pp. 1-11, vol. 1:3.
Merrifield et al., "Design and synthesis of antimicrobial peptides", Antimicrobial peptides, pp. 5-26.
Mi et al., "Characterization of a Class of Cationic Peptides Able to Facilitate Efficient Protein Transduction in Vitro and in Vivo", Molecular Therapy, Oct. 2008, pp. 339-347, vol. 2:4.
Miller et al., "A Structural Correlation Between Lentivirus Transmembrane Proteins and Natural Cytolytic Peptides", AIDS Research and Human Retroviruses, 1991, pp. 511-519, vol. 7:6.
Miller et al., "Alterations in Cell Membrane Permeability by the Lentivirus Lytic Peptide (LLP-1) of HIV-1 Transmembrane Protein", Virology, 1993, pp. 89-100, vol. 196.
Miller et al., "Identification of a Calmodulin-Binding and Inhibitory Peptide Domain in the HIV-1 Transmembrane Glycoprotein", AIDS Research and Human Retroviruses, 1993, pp. 1057-1066, vol. 9:1.
Moore et al., "Preliminary Experimental Anticancer Activity of Cecropins", Peptide Research, 1994, pp. 265-269, vol. 7:5.
Moran et al., "The diagnosis and management of prosthetic joint infections", Journal of Antimicrobial Chemotherapy, pp. iii45-iii54, vol. 65:3.
Morris et al., "A peptide carrier for the delivery of biologically active proteins into mammalian cells", Nature Biotechnology, Dec. 2021, pp. 1173-1176, vol. 19.
Novak et al., "Efficacy of the De Novo-Derived Antimicrobial Peptide WLBU2 against Oral Bacteria", Antimicrobial Agents and Chemotherapy, May 2007, pp. 1837-1839, vol. 51:5.
Palace et al., "Determination of amino acids in diverse polymeric matrices using HPLC, with emphasis on agars and agaroses", Biochimica et Biophysica Anta, 1999, pp. 509-518, vol. 1472.
Paranjape et al., "Modulation of proinflammatory activing by the engineered cationic antimicrobial peptide WLBU-2", F1000Research, 2013, pp. 1-9, vol. 2:36.
Pearson et al., "Method for Reliable Determination of Minimal Lethal Antibiotic Concentrations", Antimicrobial Agents and Chemotherapy, Nov. 1980, pp. 699-708, vol. 18:5.
Pettit et al., "Application of high throughput Alamar blue biofilm susceptibility assay to Staphylococcus aureus piofilms", Annals of Clinical Microbiology and Antimicrobials, 2009, pp. 1-7, vol. 8:28.
Phadke et al., "Selective toxicity of engineered lentivirus lytic peptides in a CF airway cell model", Peptides, 2003, pp. 1099-1107, vol. 24.
Phadke et al., "Antimicrobial Peptides in Mucosal Secretions: The Importance of Local Secretions in Mitigating Infections", Symposium: Innate Immunity and Human Milk, 2005, pp. 1289-1293.
Pulido et al., "Periprosthetic Joint Infection", Clinical Orthopedics and Related Research, Jul. 2008, pp. 1710-1715, vol. 466.
Raman et al., "Enhanced capture of bacteria and endotoxin by antimicrobial WLBU2 peptide tethered on polyethylene oxide spacers", Biointerphases, 2017, pp. 1-11, vol. 12.
Ribeiro et al., "Heme oxygenase-1 fused to a TAT peptide transduces and protects pancreatic B-cells", Biochemical and Biophysical Research Communications, 2003, pp. 876-881, vol. 305.
Robinson et al., "Anti-HIV-1 activity of indolicidin, an antimicrobial peptide from neutrophils", Journal of Leukocyte Biology, Jan. 1998, pp. 94-100, vol. 63.
Ruder et al., "Treatment of Periprosthetic Joint Infection Using Antimicrobials: Dilute Povidone-Iodine Lavage", Journal of Bone and Joint Infection, 2017, pp. 10-14, vol. 2:1.
Rushlow et al., "Lentivirus Genomic Organization: The Complete Nucleotide Sequence of the env Gene Region of Equine Infectious Anemia Virus", Virology, 1986, pp. 309-321, vol. 155.
Ryder et al., "Binding Interactions of Bacterial Lipopolysaccharide and the Cationic Amphiphilic Peptides Polymyxin B and WLBU2", Colloids of Surface B Biointerfaces, Aug. 2014, pp. 81-87, vol. 120.
Santajit et al., "Mechanisms of Antimicrobial Resistance in ESKAPE Pathogens", BioMed Research International, 2016, pp. 1-8.
Santos-Lopez et al., "Experimental evolution to identify undescribed mechanisms of resistance to a novel cationic peptide antibiotic", Dec. 2020, pp. 1-21.
Sarin et al., "Quantitative Monitoring of Solid-Phase Peptide Synthesis by the Ninhydrin Reaction", Analytical Biochemistry, 1981, pp. 147-157, vol. 117.
Schilke et al., "Identifying the selectivity of antimicrobial peptides to cell membranes by sum frequency generation spectroscopy", Biointerphases, May 2017, pp. 1-10, vol. 12:2.
Scott et al., "Biological Properties of Structurally Related a-Helical Cationic Antimicrobial Peptides", Infection and Immunity, Apr. 1999, pp. 2005-2009, vol. 67:4.
Shen et al., "Evaluation of Peptide-Mediated Transduction in Human CD34+ Cells", Human Gene Therapy, Apr. 2004, pp. 415-419, vol. 15.
Skinner et al., "Evaluation of WLBU2 Peptide and 3-0-Octyl-sn-Glycerol Lipid as Active Ingredients for a Topical Microbicide Formulation Targeting Chlamydia trachomatis", Antimicrobial Agents and Chemotherapy, Feb. 2010, pp. 627-636, vol. 54:2.
Srinivas et al., "Cytosolic Domain of the Human Immunodeficiency Virus Envelope Glycoproteins Binds to Calmodulin and Inhabits Calmodulin-regulated Proteins", The Journal of Biological Chemistry, Oct. 1993, pp. 22895-22899, vol. 268:30.
Srinivas et al., "Calmodulin Antagonists Inhibit Human Immunodeficiency Virus-Induced Cell Fusion but Not Virus Replication", AIDS Research and Human Retroviruses, 1994, pp. 1489-1496, vol. 10:11.
Swedan et al., "Synergism of cationic antimicrobial peptide WLBU2 with antibacterial agents against biofilms of multi-drug resistant Acinetobacter baumannii and Klebsiella pneuoniae", Infection and Drug Reistance, 2019, pp. 2019-2030, vol. 12.
Tam et al., "Disulfide Bond Formation in Peptides by Dimethyl Sulfoxide. Scope and Applications", Journal of the American Chemical Society, 1991, pp. 6657-6662, vol. 113.

\* cited by examiner

COMPOSITIONS COMPRISING ANTIMICROBIAL PEPTIDES

CROSS REFERENCE TO RELATED APPLICATIONS

This application is a continuation of International Patent Application No. PCT/US2020/059415, filed Nov. 6, 2020, which claims priority to U.S. Provisional Patent Application No. 62/932,609 filed Nov. 8, 2019, and U.S. Provisional Patent Application No. 63/028,636 filed May 22, 2020, the disclosure of each of which is incorporated herein by reference in its entirety.

STATEMENT REGARDING FEDERALLY SPONSORED RESEARCH

This invention was made with government support under Grant Nos. TR001856 and AR071494 awarded by the National Institutes of Health. The government has certain rights in the invention.

REFERENCE TO A SEQUENCE LISTING

The Sequence Listing associated with this application is filed in electronic format via EFS-Web and is hereby incorporated by reference into the specification in its entirety. The name of the text file containing the Sequence Listing is 6527_2107057_ST25.txt. The size of the text file is 6,088 bytes, and the text file was created on Nov. 11, 2021.

A method of treating a microbial infection in a patient is provided. A wound irrigation system also is provided.

Roughly 2 million hospital associated infections occur annually in the United States. *Staphylococcus aureus* is a major organism responsible for these infections which include surgical site and implant prosthesis related infections. Total knee arthroplasties (TKAs) are the largest major surgical procedures by volume in the US, with over 700,000 performed every year. An infected total knee arthroplasty, termed periprosthetic joint infection (PJI), occurs in 1.5-2% of patients undergoing joint replacement surgery. PJI treatment involves multiple subsequent surgical procedures and long-term antibiotic regimen. In acute PJI, debridement antibiotics and implant retention (DAIR) is a common approach. Treatment failure is over 60% and five-year mortality is approximately 25%. The majority of these infections are *S. aureus*. The high antibiotic tolerance of biofilms is increasingly recognized as a primary reason for these difficult to eradicate infections. Novel antibiotics which have better activity against biofilms are needed.

There is a need for superior compositions for treatment of biofilms, e.g. for use in surgical procedures involving implants.

SUMMARY

A pharmaceutical composition is provided comprising: a cationic antimicrobial peptide or pharmaceutically acceptable salt thereof; and a pharmaceutically acceptable aqueous carrier, wherein said pharmaceutical composition is in the form of a liquid; and wherein said pharmaceutical composition comprises a total osmolarity of from about 1 mOsm/L to about 350 mOsm/L.

A method of treating or preventing an infection in a subject in need thereof is provided. The method comprises administering a pharmaceutical composition to said subject, thereby treating or preventing said infection; wherein said pharmaceutical composition comprises: a cationic antimicrobial peptide or pharmaceutically acceptable salt thereof; and a pharmaceutically acceptable aqueous carrier, wherein said pharmaceutical composition is in the form of a liquid; and wherein said pharmaceutical composition comprises a total osmolarity of from about 1 mOsm/L to about 350 mOsm/L.

A kit is provided comprising a pharmaceutical composition is provided comprising: a cationic antimicrobial peptide or pharmaceutically acceptable salt thereof; and a pharmaceutically acceptable aqueous carrier, wherein said pharmaceutical composition is in the form of a liquid; and wherein said pharmaceutical composition comprises a total osmolarity of from about 1 mOsm/L to about 350 mOsm/L and a container.

A method of reducing microbe load in a wound in a patient is provided, comprising: washing the wound with an irrigation liquid comprising an LLP-1-derived antimicrobial peptide in a pharmaceutically acceptable aqueous carrier in an amount effective to reduce microbe load in a wound in a patient by at least 1000-fold by washing a wound for 30 minutes or less with the irrigation liquid, thereby reducing microbe load in the wound of the patient, wherein the aqueous carrier or irrigation liquid optionally is physiologically isotonic or physiologically hypotonic and/or has a pH ranging from pH 5.0 to 8.0.

A method of wound irrigation in a patient, optionally for preventing infection of the wound, is provided, comprising: washing the wound with an irrigation liquid comprising an LLP-1-derived antimicrobial peptide in a pharmaceutically acceptable aqueous carrier in an amount effective to reduce microbe load in a wound in a patient by at least 1000-fold by washing a wound for 30 minutes or less with the irrigation liquid, wherein the aqueous carrier or irrigation liquid optionally is physiologically isotonic or physiologically hypotonic or has a pH ranging from pH 5.0 to 8.0.

A method of implanting a device into a patient, optionally for preventing infection of the patient associated with implantation of the device is provided, comprising: washing the device and/or the location of device implant in the patient with an irrigation liquid comprising an LLP-1-derived antimicrobial peptide in a pharmaceutically acceptable aqueous carrier in an amount effective to reduce microbe load in a wound in a patient by at least 1000-fold by washing a wound for 30 minutes or less with the irrigation liquid, wherein the aqueous carrier or irrigation liquid optionally is physiologically isotonic or physiologically hypotonic and/or has a pH ranging from pH 5.0 to 8.0.

A lavage system is provided, comprising: an irrigation actuator configured for washing or irrigating a wound in a patient with an irrigation liquid, fluidly-connected to a reservoir comprising an irrigation liquid comprising an LLP-1-derived antimicrobial peptide in a pharmaceutically acceptable aqueous carrier in an amount effective to reduce microbe load in a wound in a patient by at least 1000-fold by washing a wound for 30 minutes or less with the irrigation liquid, wherein the aqueous carrier or irrigation liquid optionally is physiologically isotonic or physiologically hypotonic and/or has a pH ranging from pH 5.0 to 8.0.

An irrigation liquid is provided, comprising: an LLP-1-derived antimicrobial peptide in an aqueous carrier in an amount effective to reduce microbe load in a wound in a patient by at least 1000-fold by washing a wound for 30 minutes or less, wherein the irrigation liquid or aqueous carrier is physiologically hypotonic or has a pH ranging from pH 7.2 to 8.0.

A medical device is provided, packaged in the irrigation liquid comprising: an LLP-1-derived antimicrobial peptide in an aqueous carrier in an amount effective to reduce microbe load in a wound in a patient by at least 1000-fold by washing a wound for 30 minutes or less, wherein the irrigation liquid or aqueous carrier is physiologically hypotonic or has a pH ranging from pH 7.2 to 8.0.

DETAILED DESCRIPTION

Figure 1:
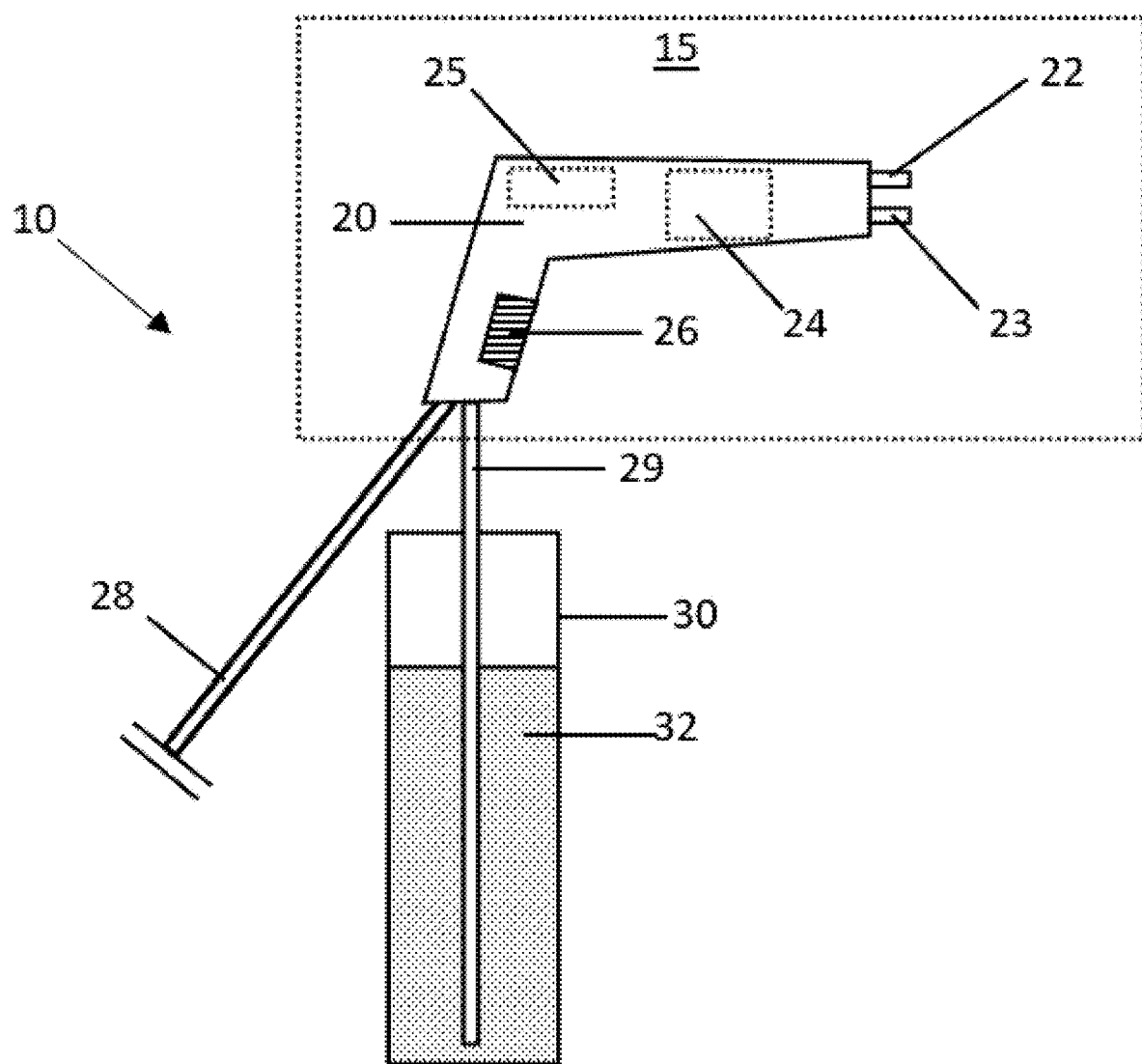
FIG. 1 is a schematic drawing of an irrigation or lavage system as described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise", or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom, including, but not limited to human beings.

As used herein, a "pharmaceutically acceptable excipient", "aqueous carrier" or "pharmaceutically acceptable aqueous carrier" refer to solvents or dispersion media, and the like, that are physiologically compatible. Examples of pharmaceutically acceptable carriers include one or more of water, saline, phosphate buffered saline, dextrose, glycerol, ethanol, and the like, as well as combinations thereof. Pharmaceutically acceptable carriers may further comprise minor amounts of auxiliary substances such as wetting or emulsifying agents, preservatives or buffers, which enhance the shelf life or effectiveness of the active agent.

An "effective amount" or "amount effective" to achieve a desirable therapeutic, pharmacological, medicinal, or physiological effect is any amount that achieves the stated purpose. For example, an amount of the antimicrobial compound, e.g. LLP-1-derived peptide effective to reduce microbe load in a wound in a patient, and/or reduce a microbial biofilm in a wound in a patient. Based on the teachings provided herein, one of ordinary skill can readily ascertain effective amounts of the elements of the described dosage form and produce a safe and effective dosage form and drug product. Examples of an effective amount of the WLBU-2 peptide compounded in a wash, irrigation, or lavage solution include 500 μg per ml (micrograms per milliliter), or 1 mg/ml (milligrams per milliliter) of solution and for WLBU-2 or other LLP-1-derived peptides may range from 1 μg/ml to 100 mg/ml, or from 100 mg/ml to 10 mg/ml. Equivalent amounts, including molar or w/v (weight/volume) equivalents, of other LLP-1-derived peptides may be utilized in the methods, systems, and devices described herein.

The term "homology" can refer to a % identity of a polypeptide to a reference polypeptide. As a practical matter, whether any particular polypeptide can be at least 50%, 60%, 70%, 80%, 85%, 90%, 92%, 95%, 96%, 97%, 98%, or 99% identical to any reference amino acid sequence of any polypeptide described herein (which may correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters can be set such that the percentage of identity is calculated over the full length of the reference amino acid sequence and that gaps in homology of up to 5% of the total number of amino acid residues in the reference sequence are allowed.

For example, in a specific embodiment the identity between a reference sequence (query sequence, i.e., a sequence of the present invention) and a subject sequence, also referred to as a global sequence alignment, may be determined using the FASTDB computer program based on the algorithm of Brutlag et al., (Comp. App. Biosci. 6:237-245 (1990)). In some embodiments, parameters for a particular embodiment in which identity is narrowly construed, used in a FASTDB amino acid alignment, can include: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction can be made to the results to take into consideration the fact that the FASTDB program does not account for N- and C-terminal truncations of the subject sequence when calculating global percent identity. For subject sequences truncated at the N- and C-termini, relative to the query sequence, the percent identity can be corrected by calculating the number of residues of the query sequence that are lateral to the N- and C-terminal of the subject sequence, which are not matched/aligned with a corresponding subject residue, as a percent of the total bases of the query sequence. A determination of whether a residue is matched/aligned can be determined by results of the FASTDB sequence alignment. This percentage can be then subtracted from the percent identity, calculated by the FASTDB program using the specified parameters, to arrive at a final percent identity score. This final percent identity score can be used for the purposes of this embodiment. In some embodiments, only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence are considered for this manual correction. For example, a 90 amino acid residue subject sequence can be aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/ aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

The terms "co-administration", "administered in combination with" and their grammatical equivalents or the like, as used herein, can encompass administration of selected therapeutic agents to a subject, and can include treatment regimens in which agents are administered by the same or different route of administration or at the same or different times. In some embodiments, a peptide disclosed herein can be co-administered with other agents. These terms can encompass administration of two or more agents to a subject so that both agents and/or their metabolites are present in the subject at the same time. They can include simultaneous administration, administration at different times, and/or administration in a composition in which both agents are present. Thus, in some embodiments, a peptide and an additional agent(s) can be administered in a single composition. In some embodiments, a peptide and an additional agent(s) can be admixed in the composition. In some embodiments, a same peptide or agent can be administered via a combination of different routes of administration. In some embodiments, each agent administered can be in a therapeutically effective amount.

The antimicrobial peptides, such as the LLP-1-derived peptides as described herein, including WLBU-2, may be formulated or compounded into, e.g., dissolved into or otherwise dispersed into, an irrigation liquid drug product with any suitable, e.g. pharmaceutically-acceptable, aqueous solution, carrier, or excipient (collectively, aqueous carrier), such as, without limitation: water; buffer solutions; salt solutions, such as saline; buffered salt solutions, such as phosphate-buffered saline; among others as are known in the pharmaceutical and compounding arts. The irrigation liquid, may be formulated to reduce microbial load or a biofilm in a wound, e.g., with 3-logs or greater (1000-fold or greater) decrease in microbe load, in 30 minutes or less, 20 minutes or less, 15 minutes or less, 10 minutes or less, or 5 minutes or less of contact time with a biofilm or wound. The irrigation liquid may be physiologically hypertonic, isotonic, or hypotonic. The irrigation liquid may be slightly acidic, neutral, or alkaline, e.g., ranging from pH 4.0 to pH 11.0, including increments therebetween, such as 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or 11.0, including increments therebetween, including increments therebetween. The aqueous carrier may be physiologically isotonic, as with lactated Ringer's solution or normal saline (0.9% w/v), or physiologically hypotonic (sub-physiologic osmolarity or osmolality), such as modified versions of either lactated Ringer's solution or normal saline diluted, for example, with water. The physiologically hypotonic carrier may have a pH greater than 5.0, or may be alkaline, that is, having a pH of greater than 7.0. The aqueous carrier or the irrigation liquid may have a total osmolarity ranging from 1 milliosmoles per one liter (mOsm/L) to 350 mOsm/L, e.g., from 50 mOsm/L to 300 mOsm/L or from 2 mOsm/L to 200 mOsm/L. The aqueous carrier or the irrigation liquid may have a total ionic strength between 0.01 molar (M) and 0.4 M, e.g., from 0.02 M and 0.2 M. The aqueous carrier may be selected to have an alkaline pH, or yield an alkaline pH in the irrigation liquid, such as a pH ranging from 7.2 to 8.0. The pH of the irrigation liquid may be adjusted to have an alkaline pH through the addition of a base, such as ammonium hydroxide, sodium hydroxide, magnesium hydroxide, sodium carbonate, or combinations thereof to the aqueous carrier. Higher pH values for the product are contemplated, but may prove to be too alkaline and therefore too damaging for use in wound irrigation. The carrier may be physiologically hypotonic, meaning it has, or yields an irrigation liquid having, a lower concentration of solutes as compared to a cytosol of a cell in a normal patient, or as compared to blood, plasma, serum, or lymph in a normal patient. The carrier or irrigation liquid may be both physiologically hypotonic and alkaline, e.g., having a pH ranging from 7.2 to 8.0. Examples of suitable alkaline pH values for the drug product include 7.2, 7.3, 7.4, 7.5, 7.6, 7.7, 7.8, 7.9, or 8.0, including increments therebetween, or pH ranges such as from 7.4 to 8.0, or from 7.5 to 8.0.

Drug products, e.g., wash, irrigation, or lavage liquids or solutions, as described herein, are useful, and may be used, in a surgical setting and, unlike prior irrigation solutions, can be used intraoperatively, meaning they can be used during a single surgical procedure without significant delay, or inactive waiting periods. That is, they effectively reduce microbial load or a biofilm in a wound, e.g., with 3-logs or greater (1000-fold or greater) decrease in microbe load, in 30 minutes or less, 20 minutes or less, 15 minutes or less, 10 minutes or less, or 5 minutes or less of contact time with a biofilm or wound. The drug product described herein, for example comprising a described antimicrobial peptide, and, in some instances, one or both of an alkaline pH or a sub-physiological osmolarity or osmolality, can achieve such rapid reductions of microbial load or biofilm when used for wound wash, irrigation, or lavage.

By "reduce microbe load" or to "reduce a biofilm" in a wound, or like phrases, it is meant to lower the overall number of living microbes in a wound. "Microbe" includes, without limitation, bacteria, fungi, protozoans, and viruses and does not refer to normal, eukaryotic, cells of a patient. A microbe may be considered a pathogen or pathogenic in the context of the present disclosure.

A therapeutic agent is any compound or composition that is delivered to a patient to achieve a desired effect, such as a beneficial, treatment, or curative effect. Therapeutic agents include proteins, such as polypeptides or proteins. In the context of the present disclosure, therapeutic agents are peptides having antimicrobial activity ("antimicrobial peptides"). The antimicrobial peptides may be derived from, and are analogs of, the LLP-1 peptide parent sequence corresponding to amino acids 828-856 of the HIV-I viral isolate HXB2R Env, including SA-5 (SEQ ID NO: 1), LSA-5 (SEQ ID NO: 2) and WLSA-5 (SEQ ID NO: 3) (see Table 1 below). The antimicrobial activity of other LLP-1 peptide analogues has been previously described (see, Tencza et al., 1999, Journal of Antimicrobial Chemotherapy 44:33-41, U.S. Pat. No. 5,714,577 of Montelaro et al. and U.S. Pat. No. 5,945,507 of Montelaro et al., the disclosures of which are incorporated herein by reference). The antimicrobial peptides may be LLP-1 analogs having modifications based on the following principles: (i) optimizing amphipathicity, (ii) substituting arginine (Arg) on the charged face and/or valine (Val) or tryptophan (Trp) on the hydrophobic face with another amino acid, and (iii) increasing peptide length, such as, without limitation LBU-1 (SEQ ID NO: 4); LBU-2 (SEQ ID NO: 5); LBU-3 (SEQ ID NO: 6); LBU-3.5 (SEQ ID NO: 7); LBU-4 (SEQ ID NO: 8); WLBU-1 (SEQ ID NO: 9); WLBU-2 (SEQ ID NO: 10); WLBU-3 (SEQ ID NO: 11); or WLBU-4 (SEQ ID NO: 12); see Table 1). Amino acid sequences are provided, left-to-right, from their N-terminus to their C-terminus.

TABLE 1

| | | |
|---|---|---|
| SA-5: | RVIRV VQRAC RAIRH IVRRI RQGLR RIL | (SEQ ID NO: 1) |
| LSA-5: | RVIRV VQRAC RAIRH IVRRI RQGLR RILRV V | (SEQ ID NO: 2) |
| WLSA-5: | RWIRV VQRWC RAIRH IWRRI RQGLR RWLRV V | (SEQ ID NO: 3) |
| LBU-1: | RVVRV VRRVV RR | (SEQ ID NO: 4) |
| LBU-2: | RRVVR RVRRV VRRVV RVVRR VVRR | (SEQ ID NO: 5) |
| LBU-3: | VRVV RRVVR VVRRV VRRVR RVVRR VVRVV RRVVRR | (SEQ ID NO: 6) |
| LBU-3.5: | RRVVR RVRRV VRRVV RVVRR VVRRV RRVVR RVVRV VRRVV RR | (SEQ ID NO: 7) |
| LBU-4: | RVVRV VRRVV RRVRR VVRRV VRVVR RVVRR VRRVV RRVVR VVRRV VRR | (SEQ ID NO: 8) |
| WLBU-1 | RVVRV VRRWV RR | (SEQ ID NO: 9) |
| WLBU-2 | RRWVR RVRRV WRRVV RVVRR WVRR | (SEQ ID NO: 10) |
| WLBU-3 | VRRVW RRVVR VVRRW VRRVR RVWRR VVRVV RRWVR R | (SEQ ID NO: 11) |
| WLBU-4 | RVVRV VRRWV RRVRR VWRRV VRVVR RWVRR VRRVW RRVVR VVRRW RVV | (SEQ ID NO: 12) |

The antimicrobial peptides described herein are highly inhibitory to microorganisms under physiologic salt concentrations and other conditions and function in the presence of synovial fluid, demonstrating only minimal toxicity in animal models. As a result, the antimicrobial agents may be defined as selective antimicrobial agents. The antimicrobial peptides include arginine/tryptophan-rich peptides as presented in Table 2, below. The peptides of SEQ ID NOs: 1-16 are described in U.S. Pat. No. 8,071,540, and their broad-spectrum antimicrobial activity is demonstrated therein and in subsequent publications.

TABLE 2

| Peptide | Sequence | Comments |
|---|---|---|
| WR6 | RRWWRR | SEQ ID NO: 13 |
| WR12 | RWWRWWRRWWRR | SEQ ID NO: 14 |
| WR18 | WRRWWRRWWRWWRRWWRR | SEQ ID NO: 15 |
| WR24 | RRWWRRWRRWWRRWWRWWRRWWRR | SEQ ID NO: 16 |

Additional LLP-1-derived antimicrobial peptides are disclosed in U.S. Pat. No. 6,887,847 and in International Patent Application Publication No. 2018/160997, both of which are incorporated herein by reference for their disclosure of LLP-1-derived antimicrobial peptides.

A method of treating an infection, reducing a microbial load in a wound, or irrigating a wound in a patient is provided. A wound may be traumatic or surgical, e.g., caused by a surgeon in the course of a surgical procedure to expose an infected implant or infected tissue, as in an abscess. The method comprises washing a wound or implant, optionally comprising a microbe or biofilm, with a wash, irrigation, or lavage solution, that is, an irrigation liquid as described herein, comprising an LLP-1-derived antimicrobial peptide, such as a peptide of one of SEQ ID NOS: 1-16, for example WLBU-2. The composition may be alkaline (having a pH of at least 7.2) and/or sub-physiologically hypotonic (e.g., having an osmolarity, osmolality, or ionic strength less than that of blood or normal (0.9% w/v) saline). The washing reduces or eliminates the microbial load of the wound or implant.

Contact time for the irrigation liquid comprising the antimicrobial peptide, for example for a physiologically hypoosmotic solution, or a solution having an alkaline pH and/or a sub-physiological osmolarity is suitable for use in a surgical setting, exhibiting 3-logs or greater decrease in microbe load in 30 minutes or less, for example in 20 minutes or less, 15 minutes or less, 10 minutes or less, or 5 minutes or less. As compared to previously-described compositions, even those including the described LLP-1-derived peptides such as those of SEQ ID NOS: 1-16, the irrigation liquids described herein, e.g. the alkaline and/or hypotonic solutions described herein, decrease microbial load so quickly that they can be used in a surgical setting without significant wait time.

There are multiple methods of washing or irrigating a wound or implant, including soaking, low-pressure lavage with solution gravity-fed from, e.g., an IV bag, or high-pressure lavage in which a wash solution is pumped or pulsed into a wound. The irrigation solution may be used to wash or irrigate a wound or implant by any useful method, including soaking or actively jetting, spraying, or pulsing according to any useful method, e.g., as are known in the surgical arts, including, without limitation: pouring the irrigation liquid, gravity dripping the irrigation liquid, spraying the irrigation liquid, e.g. with a medical syringe, pumping or pulsing the liquid with a lavage device such as a pulse lavage device. Once initially contacted with the wound or implant, the irrigation solution is contacted for a suitable duration to sufficiently reduce microbial load or biofilm, e.g., 1, 2, 5, 10, 15, 20, 25, or 30 minutes, during which time the irrigation solution may be allowed to remain, dwell, or soak in place for the duration of the contact period or administered continuously or non-continuously, and when not being delivered, it is allowed to remain, dwell, or soak in place for the duration of the contact period.

In one example, a knee implant, or other orthopedic implant, may become infected. In current practice, the infected tissue is debrided and the partially- or fully-exposed implant is irrigated with a saline solution or another physiological solution. Because traditional methods of cleaning up infected implants and surrounding tissue are ineffective at sufficient or complete removal of microbes, antibiotics are administered to the patient. With the increased risk of antibiotic resistance in such microbes, antibiotic treatment may be either difficult or ineffective. The compositions and methods described herein are able to significantly reduce microbe load or to eliminate microbe load in a short time period (e.g., in less than 30 minutes or faster), and, as such, can reduce or eliminate infection following treatment, and/or reduce the difficulty of post-surgical infections.

An implant may be any foreign body inserted temporarily or permanently in a patient, such as an orthopedic implant, a drainage tube, a cannula or catheter, such as for use in dialysis, a stent, a pacemaker, or any other device.

Also provided herein is a wash, irrigation, or lavage system for delivering to a patient, e.g., to a wound of a patient, a wash, irrigation, or lavage solution as described herein comprising an antimicrobial peptide. A pulse lavage system 10 is depicted schematically in FIG. 1 comprising an irrigation actuator for delivering an irrigation liquid for e.g., wound irrigation. The system 10 comprises an irrigation actuator subsystem 15 (actuator) comprising a body 20 having a suction nozzle 22 and an outlet nozzle 23 through which fluid is pumped by the body 20. The body 20 comprises one or more internal pumps (24, shown schematically in phantom) that may be battery powered by an internal battery (25, shown schematically in phantom) or powered externally, e.g. using a power supply connected to the body via a power adaptor (not shown), and configured to pump liquid through the outlet nozzle 23 as a stream, spray or jet in a continuous or pulsed manner. Operation of the pump 24 is controlled by the trigger 26, which may act in an on/off fashion, or may stepwise, linearly, or non-linearly control pumping speed. A first tube 28 is provided and is fluidly coupled to the suction nozzle 22, and is configured such that a vacuum is applied to the first tube 28 to suck liquid and debris through the suction nozzle 22. A valve (not shown) may be inserted in-line between the first tube 28 and the suction nozzle 22, to control suction through the suction nozzle 22, and which may be or may act independently, e.g., via a second trigger incorporated into the body 20 or concurrently with the action of the trigger 26. Trigger 26, and any additional triggers or controls may be external to the body, for example in the form of foot switches, pedals, or actuators. A second tube 29 is depicted and is coupled to the pump 24 and outlet nozzle 23. The system 10 also comprises a reservoir 30, such as a bottle or bag (e.g. an i.v. bag) comprising a wash, irrigation, or lavage solution 32 comprising an antimicrobial peptide as described herein. The second tube 29 is configured within the reservoir 30 to supply solution 32 to the pump of the body 20 to deliver the solution 32 through the outlet nozzle 23. The suction nozzle 22 and the outlet nozzle 24 each, independently, may have any useful shape or configuration as is appropriate for a pulsed lavage device as are broadly-known. Alternatively, the actuator may only comprise an outlet nozzle, with suction being applied independently of the lavage system, e.g., using an independent, external vacuum supply and trap connected to a separate suction device comprising a suction nozzle. The system 10 of FIG. 1 is merely exemplary. Variations in structure and design of lavage devices are broadly-known in the art, such as a sprayer-driven, or pump-driven irrigation device, optionally comprising a suction feature for removing liquid and tissue, such as, for example and without limitation, Simpulse™ VariCare™ Suction Irrigator (Davol, Inc.), Interpulse pulsed lavage system (Stryker), or the IGLOO® wound irrigation device (Bionix).

Dosage

In some cases, a peptide, salt thereof, or pharmaceutical composition comprising a peptide or salt thereof described herein can be administered at a dose of from about 1 mg to about 1000 mg, from about 5 mg to about 1000 mg, from about 10 mg to about 1000 mg, from about 15 mg to about 1000 mg, from about 20 mg to about 1000 mg, from about 25 mg to about 1000 mg, from about 30 mg to about 1000 mg, from about 35 mg to about 1000 mg, from about 40 mg to about 1000 mg, from about 45 mg to about 1000 mg, from about 50 mg to about 1000 mg, from about 55 mg to about 1000 mg, from about 60 mg to about 1000 mg, from about 65 mg to about 1000 mg, from about 70 mg to about 1000 mg, from about 75 mg to about 1000 mg, from about 80 mg to about 1000 mg, from about 85 mg to about 1000 mg, from about 90 mg to about 1000 mg, from about 95 mg to about 1000 mg, from about 100 mg to about 1000 mg, from about 150 mg to about 1000 mg, from about 200 mg to about 1000 mg, from about 250 mg to about 1000 mg, from about 300 mg to about 1000 mg, from about 350 mg to about 1000 mg, from about 400 mg to about 1000 mg, from about 450 mg to about 1000 mg, from about 500 mg to about 1000 mg, from about 550 mg to about 1000 mg, from about 600 mg to about 1000 mg, from about 650 mg to about 1000 mg, from about 700 mg to about 1000 mg, from about 750 mg to about 1000 mg, from about 800 mg to about 1000 mg, from about 850 mg to about 1000 mg, from about 900 mg to about 1000 mg, or from about 950 mg to about 1000 mg.

In some cases, a formulation described herein can be in unit dose form. In some cases, the unit dose can be from about 0.001 µg/kg to about 1000 mg/kg, from about 0.001 µg/kg to about 900 mg/kg, from about 0.001 µg/kg to about 800 mg/kg, from about 0.001 µg/kg to about 700 mg/kg, from about 0.001 µg/kg to about 600 mg/kg, from about 0.001 µg/kg to about 500 mg/kg, from about 0.001 µg/kg to about 400 mg/kg, from about 0.001 µg/kg to about 300 mg/kg, from about 0.001 µg/kg to about 200 mg/kg, from about 0.001 µg/kg to about 100 mg/kg, from about 0.001 µg/kg to about 90 mg/kg, from about 0.001 µg/kg to about 80 mg/kg, from about 0.001 µg/kg to about 70 mg/kg, from about 0.001 µg/kg to about 60 mg/kg, from about 0.001 µg/kg to about 50 mg/kg, from about 0.001 µg/kg to about 40 mg/kg, from about 0.001 µg/kg to about 30 mg/kg, from about 0.001 µg/kg to about 20 mg/kg, from about 0.001 µg/kg to about 10 mg/kg, from about 0.001 µg/kg to about 9 mg/kg, from about 0.001 µg/kg to about 8 mg/kg, from about 0.001 µg/kg to about 7 mg/kg, from about 0.001 µg/kg to about 6 mg/kg, from about 0.001 µg/kg to about 5 mg/kg, from about 0.001 µg/kg to about 4 mg/kg, from about 0.001 µg/kg to about 3 mg/kg, from about 0.001 µg/kg to about 2 mg/kg, from about 0.001 µg/kg to about 1 mg/kg, from about 0.001 mg/kg to about 1000 mg/kg, from about 0.001 mg/kg to about 900 mg/kg, from about 0.001 mg/kg to about 800 mg/kg, from about 0.001 mg/kg to about 700 mg/kg, from about 0.001 mg/kg to about 600 mg/kg, from about 0.001 mg/kg to about 500 mg/kg, from about 0.001 mg/kg to about 400 mg/kg, from about 0.001 mg/kg to about 300 mg/kg, from about 0.001 mg/kg to about 200 mg/kg, from about 0.001 mg/kg to about 100 mg/kg, from about 0.001 mg/kg to about 90 mg/kg, from about 0.001 mg/kg to about 80 mg/kg, from about 0.001 mg/kg to about 70 mg/kg, from about 0.001 mg/kg to about 60 mg/kg, from about 0.001 mg/kg to about 50 mg/kg, from about 0.001 mg/kg to about 40 mg/kg, from about 0.001 mg/kg to about 30 mg/kg, from about 0.001 mg/kg to about 20 mg/kg, from about 0.001 mg/kg to about 10 mg/kg, from about 0.001 mg/kg to about 9 mg/kg, from about 0.001 mg/kg to about 8 mg/kg, from about 0.001 mg/kg to about 7 mg/kg, from about 0.001 mg/kg to about 6 mg/kg, from about 0.001 mg/kg to about 5 mg/kg, from about 0.001 mg/kg to about 4 mg/kg, from about 0.001 mg/kg to about 3 mg/kg, from about 0.001 mg/kg to about 2 mg/kg, from about 0.001 mg/kg to about 1 mg/kg, from about 0.001 mg/kg to about 0.9 mg/kg, from about 0.001 mg/kg to about 0.8 mg/kg, from about 0.001 mg/kg to about 0.7 mg/kg, from about 0.001 mg/kg to about 0.6 mg/kg, from about 0.001 mg/kg to about 0.5 mg/kg, from about 0.001 mg/kg to about 0.4 mg/kg, from about 0.001 mg/kg to about 0.3 mg/kg, from about 0.001 mg/kg to about 0.2 mg/kg, or from about 0.001 mg/kg to about 0.1 mg/kg of peptide or pharmaceutically acceptable salt thereof to weight of subject. In some cases, a unit dose can be about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10 mg/kg, about 10.1 mg/kg, about 10.2 mg/kg, about 10.3 mg/kg, about 10.4 mg/kg, about 10.5 mg/kg, about 10.6 mg/kg, about 10.7 mg/kg, about 10.8 mg/kg, about 10.9 mg/kg, about 11 mg/kg, about 11.1 mg/kg, about 11.2 mg/kg, about 11.3 mg/kg, about 11.4 mg/kg, about 11.5 mg/kg, about 11.6 mg/kg, about 11.7 mg/kg, about 11.8 mg/kg, about 11.9 mg/kg, about 12 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, about 15.9 mg/kg, about 16 mg/kg, about 16.1 mg/kg, about 16.2 mg/kg, about 16.3 mg/kg, about 16.4 mg/kg, about 16.5 mg/kg, about 16.6 mg/kg, about 16.7 mg/kg, about 16.8 mg/kg, about 16.9 mg/kg, about 17 mg/kg, about 17.1 mg/kg, about 17.2 mg/kg, about 17.3 mg/kg, about 17.4 mg/kg, about 17.5 mg/kg, about 17.6 mg/kg, about 17.7 mg/kg, about 17.8 mg/kg, about 17.9 mg/kg, about 18 mg/kg, about 18.1 mg/kg, about 18.2 mg/kg, about 18.3 mg/kg, about 18.4 mg/kg, about 18.5 mg/kg, about 18.6 mg/kg, about 18.7 mg/kg, about 18.8 mg/kg, about 18.9 mg/kg, about 19 mg/kg, about 19.1 mg/kg, about 19.2 mg/kg, about 19.3 mg/kg, about 19.4 mg/kg, about 19.5 mg/kg, about 19.6 mg/kg, about 19.7 mg/kg, about 19.8 mg/kg, about 19.9 mg/kg, about 20 mg/kg, about 20.1 mg/kg, about 20.2 mg/kg, about 20.3 mg/kg, about 20.4 mg/kg, about 20.5 mg/kg, about 20.6 mg/kg, about 20.7 mg/kg, about 20.8 mg/kg, about 20.9 mg/kg, about 21 mg/kg, about 21.1 mg/kg, about 21.2 mg/kg, about 21.3 mg/kg, about 21.4 mg/kg, about 21.5 mg/kg, about 21.6 mg/kg, about 21.7 mg/kg, about 21.8 mg/kg, about 21.9 mg/kg, about 22 mg/kg, about 22.1 mg/kg, about 22.2 mg/kg, about 22.3 mg/kg, about 22.4 mg/kg, about 22.5 mg/kg, about 22.6 mg/kg, about 22.7 mg/kg, about 22.8 mg/kg, about 22.9 mg/kg, about 23 mg/kg, about 23.1 mg/kg, about 23.2 mg/kg, about 23.3 mg/kg, about 23.4 mg/kg, about 23.5 mg/kg, about 23.6 mg/kg, about 23.7 mg/kg, about 23.8 mg/kg, about 23.9 mg/kg, about 24 mg/kg, about 24.1 mg/kg, about 24.2 mg/kg, about 24.3 mg/kg, about 24.4 mg/kg, about 24.5 mg/kg, about 24.6 mg/kg, about 24.7 mg/kg, about 24.8 mg/kg, about 24.9 mg/kg, about 25 mg/kg, about 25.1 mg/kg, about 25.2 mg/kg, about 25.3 mg/kg, about 25.4 mg/kg, about 25.5 mg/kg, about 25.6 mg/kg, about 25.7 mg/kg, about 25.8 mg/kg, about 25.9 mg/kg, about 26 mg/kg, about 26.1 mg/kg, about 26.2 mg/kg, about 26.3 mg/kg, about 26.4 mg/kg, about 26.5 mg/kg, about 26.6 mg/kg, about 26.7 mg/kg, about 26.8 mg/kg, about 26.9 mg/kg, about 27 mg/kg, about 27.1 mg/kg, about 27.2 mg/kg, about 27.3 mg/kg, about 27.4 mg/kg, about 27.5 mg/kg, about 27.6 mg/kg, about 27.7 mg/kg, about 27.8 mg/kg, about 27.9 mg/kg, about 28 mg/kg, about 28.1 mg/kg, about 28.2 mg/kg, about 28.3 mg/kg, about 28.4 mg/kg, about 28.5 mg/kg, about 28.6 mg/kg, about 28.7 mg/kg, about 28.8 mg/kg, about 28.9 mg/kg, about 29 mg/kg, about 29.1 mg/kg, about 29.2 mg/kg, about 29.3 mg/kg, about 29.4 mg/kg, about 29.5 mg/kg, about 29.6 mg/kg, about 29.7 mg/kg, about 29.8 mg/kg, about 29.9 mg/kg, about 30 mg/kg, about 30.1 mg/kg, about 30.2 mg/kg, about 30.3 mg/kg, about 30.4 mg/kg, about 30.5 mg/kg, about 30.6 mg/kg, about 30.7 mg/kg, about 30.8 mg/kg, about 30.9 mg/kg, about 31 mg/kg, about 31.1 mg/kg, about 31.2 mg/kg, about 31.3 mg/kg, about 31.4 mg/kg, about 31.5 mg/kg, about 31.6 mg/kg, about 31.7 mg/kg, about 31.8 mg/kg, about 31.9 mg/kg, about 32 mg/kg, about 32.1 mg/kg, about 32.2 mg/kg, about 32.3 mg/kg, about 32.4 mg/kg, about 32.5 mg/kg, about 32.6 mg/kg, about 32.7 mg/kg, about 32.8 mg/kg, about 32.9 mg/kg, about 33 mg/kg, about 33.1 mg/kg, about 33.2 mg/kg, about 33.3 mg/kg, about 33.4 mg/kg, about 33.5 mg/kg, about 33.6 mg/kg, about 33.7 mg/kg, about 33.8 mg/kg, about 33.9 mg/kg, about 34 mg/kg, about 34.1 mg/kg, about 34.2 mg/kg, about 34.3 mg/kg, about 34.4 mg/kg, about 34.5 mg/kg, about 34.6 mg/kg, about 34.7 mg/kg, about 34.8 mg/kg, about 34.9 mg/kg, about 35 mg/kg, about 35.1 mg/kg, about 35.2 mg/kg, about 35.3 mg/kg, about 35.4 mg/kg, about 35.5 mg/kg, about 35.6 mg/kg, about 35.7 mg/kg, about 35.8 mg/kg, about 35.9 mg/kg, about 36 mg/kg, about 36.1 mg/kg, about 36.2 mg/kg, about 36.3 mg/kg, about 36.4 mg/kg, about 36.5 mg/kg, about 36.6 mg/kg, about 36.7 mg/kg, about 36.8 mg/kg, about 36.9 mg/kg, about 37 mg/kg, about 37.1 mg/kg, about 37.2 mg/kg, about 37.3 mg/kg, about 37.4 mg/kg, about 37.5 mg/kg, about 37.6 mg/kg, about 37.7 mg/kg, about 37.8 mg/kg, about 37.9 mg/kg, about 38 mg/kg, about 38.1 mg/kg, about 38.2 mg/kg, about 38.3 mg/kg, about 38.4 mg/kg, about 38.5 mg/kg, about 38.6 mg/kg, about 38.7 mg/kg, about 38.8 mg/kg, about 38.9 mg/kg, about 39 mg/kg, about 39.1 mg/kg, about 39.2 mg/kg, about 39.3 mg/kg, about 39.4 mg/kg, about 39.5 mg/kg, about 39.6 mg/kg, about 39.7 mg/kg, about 39.8 mg/kg, about 39.9 mg/kg, about 40 mg/kg, about 40.1 mg/kg, about 40.2 mg/kg, about 40.3 mg/kg, about 40.4 mg/kg, about 40.5 mg/kg, about 40.6 mg/kg, about 40.7 mg/kg, about 40.8 mg/kg, about 40.9 mg/kg, about 41 mg/kg, about 41.1 mg/kg, about 41.2 mg/kg, about 41.3 mg/kg, about 41.4 mg/kg, about 41.5 mg/kg, about 41.6 mg/kg, about 41.7 mg/kg, about 41.8 mg/kg, about 41.9 mg/kg, about 42 mg/kg, about 42.1 mg/kg, about 42.2 mg/kg, about 42.3 mg/kg, about 42.4 mg/kg, about 42.5 mg/kg, about 42.6 mg/kg, about 42.7 mg/kg, about 42.8 mg/kg, about 42.9 mg/kg, about 43 mg/kg, about 43.1 mg/kg, about 43.2 mg/kg, about 43.3 mg/kg, about 43.4 mg/kg, about 43.5 mg/kg, about 43.6 mg/kg, about 43.7 mg/kg, about 43.8 mg/kg, about 43.9 mg/kg, about 44 mg/kg, about 44.1 mg/kg, about 44.2 mg/kg, about 44.3 mg/kg, about 44.4 mg/kg, about 44.5 mg/kg, about 44.6 mg/kg, about 44.7 mg/kg, about 44.8 mg/kg, about 44.9 mg/kg, about 45 mg/kg, about 45.1 mg/kg, about 45.2 mg/kg, about 45.3 mg/kg, about 45.4 mg/kg, about 45.5 mg/kg, about 45.6 mg/kg, about 45.7 mg/kg, about 45.8 mg/kg, about 45.9 mg/kg, about 46 mg/kg, about 46.1 mg/kg, about 46.2 mg/kg, about 46.3 mg/kg, about 46.4 mg/kg, about 46.5 mg/kg, about 46.6 mg/kg, about 46.7 mg/kg, about 46.8 mg/kg, about 46.9 mg/kg, about 47 mg/kg, about 47.1 mg/kg, about 47.2 mg/kg, about 47.3 mg/kg, about 47.4 mg/kg, about 47.5 mg/kg, about 47.6 mg/kg, about 47.7 mg/kg, about 47.8 mg/kg, about 47.9 mg/kg, about 48 mg/kg, about 48.1 mg/kg, about 48.2 mg/kg, about 48.3 mg/kg, about 48.4 mg/kg, about 48.5 mg/kg, about 48.6 mg/kg, about 48.7 mg/kg, about 48.8 mg/kg, about 48.9 mg/kg, about 49 mg/kg, about 49.1 mg/kg, about 49.2 mg/kg, about 49.3 mg/kg, about 49.4 mg/kg, about 49.5 mg/kg, about 49.6 mg/kg, about 49.7 mg/kg, about 49.8 mg/kg, about 49.9 mg/kg, or about 50.0 mg/kg.

Kits

Disclosed herein are kits. A kit can comprise a peptide, salt thereof, formulation, or pharmaceutical composition comprising a peptide described herein. In some aspects, a peptide, formulation, or composition can be packaged in a container. In some aspects, a kit can further comprise instructions that direct administration of a unit dose of a peptide or formulation to a subject. In some aspects, a kit can comprise a peptide disclosed herein and instructions for the use thereof.

Methods of making a kit can include placing a peptide, salt thereof, formulation, or pharmaceutical composition comprising a peptide described herein in a container for packaging. A method can further comprise an inclusion of instructions for use. In some cases, instructions for use can direct administration of a unit dose of a peptide or formulation to a subject.

Methods of Administration

Administration can orally, rectally, or parenterally, in formulations containing conventionally acceptable carriers, adjuvants, and vehicles as desired. Administration can also be intra-arterial, intravenous, intramuscular, oral, subcutaneous, intranasal, inhalable, or any combination thereof. In some embodiments, administration can be injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural, subcutaneous, inhalational, transdermal, transmucosal, sublingual, buccal and topical (including epicutaneous, dermal, enema, eye drops, ear drops, intranasal, vaginal) administration. In some exemplary embodiments, a route of administration can be via an injection such as an intramuscular, intravenous, subcutaneous, or intraperitoneal injection.

Administration of a peptide, salt thereof, or a pharmaceutical composition comprising a peptide comprising a peptide or salt thereof to a subject can be used to at least partially ameliorate a bacterial infection in a subject. Administration of a peptide, salt, or pharmaceutical composition comprising a peptide can be performed for a treatment duration of at least about at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days consecutive or nonconsecutive days. In some cases, a treatment duration can be from about 1 to about 30 days, from about 2 to about 30 days, from about 3 to about 30 days, from about 4 to about 30 days, from about 5 to about 30 days, from about 6 to about 30 days, from about 7 to about 30 days, from about 8 to about 30 days, from about 9 to about 30 days, from about 10 to about 30 days, from about 11 to about 30 days, from about 12 to about 30 days, from about 13 to about 30 days, from about 14 to about 30 days, from about 15 to about 30 days, from about 16 to about 30 days, from about 17 to about 30 days, from about 18 to about 30 days, from about 19 to about 30 days, from about 20 to about 30 days, from about 21 to about 30 days, from about 22 to about 30 days, from about 23 to about 30 days, from about 24 to about 30 days, from about 25 to about 30 days, from about 26 to about 30 days, from about 27 to about 30 days, from about 28 to about 30 days, or from about 29 to about 30 days.

Administration of a peptide, salt, or pharmaceutical composition comprising a peptide can be performed at least 1, 2, 3, 4, 5, 6, 7, 8, 9, 10, 11, 12, 13, 14, 15, 16, 17, 18, 19, 20, 21, 22, 23, or 24 times a day. In some embodiments, a peptide, salt, or pharmaceutical composition comprising a peptide can be administered consecutively. In some embodiments, a peptide, salt, or pharmaceutical composition comprising a peptide can be administered non-consecutively.

In some cases, administration of a peptide, salt, or pharmaceutical composition comprising a peptide can be performed at least 1, 2, 3, 4, 5, 6, 7, 8, 9, 10, 11, 12, 13, 14, 15, 16, 17, 18, 19, 20, or 21 times a week. In some cases, administration of a peptide, salt, or pharmaceutical composition comprising a peptide can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

In some cases, a peptide, salt, or pharmaceutical composition comprising a peptide can be administered in combination with an additional antibiotic, antifungal or an antiviral agent described herein. Administration of a peptide, salt, or pharmaceutical composition comprising a peptide can be performed concurrently with an additional antibiotic, antifungal or an antiviral agent described herein. In some embodiments, administration of a peptide, salt, or pharmaceutical composition comprising a peptide can be performed as the secondary treatment to an additional antibiotic, antifungal or an antiviral agent described herein.

In some exemplary embodiments, an additional antibiotic can be selected from the group consisting of: silver nitrate, Ceftobiprole, Ceftaroline, Clindamycin, Cefazolin, Dalbavancin, Daptomycin, Linezolid, Mupirocin, Oritavancin, Tedizolid, Telavancin, Tigecycline, Vancomycin, an Aminoglycoside, a Carbapenem, Ceftazidime, Cefepime, Ceftobiprole, a Fluoroquinolone, Piperacillin, Ticarcillin, Linezolid, a Streptogramin, Tigecycline, Daptomycin, a salt of any of these, and any combination thereof. In some cases, an antiviral compound can be selected from the group consisting of: Acyclovir, Brivudine, Docosanol, Famciclovir, Idoxuridine, Penciclovir, Trifluridine, Valacyclovir, Amantadine, Rimantadine, a neuraminidase inhibitor, Oseltamivir, Zanamivir, a salt of any of these, and any combination thereof.

In some exemplary embodiments, a peptide can be administered to a subject to treat a *Staphylococcus aureus* infection for a treatment duration of from about 5 days to about 30 days. Secession of treatment can be determined by an arresting of growth of a pathogen, or an amelioration of symptoms associated with an infection.

Example 1

WLBU-2 is an example of synthetically engineered cationic peptide based on optimization of the naturally occurring antimicrobial peptide LL37 (See, e.g., U.S. Pat. No. 8,071,540). Potential indications of its use include intraoperative delivery for DAIR and two-stage procedures in PJI based on its ability to rapidly eliminate antibiotic tolerant biofilm from implant surfaces and broad-spectrum activity against ESKAPE (*Enterococcus faecium, Staphylococcus aureus, Klebsiella pneumoniae, Acinetobacter baumannii, Pseudomonas aeruginosa,* and *Enterobacter* species) or *Escherichia coli* pathogens (See, e.g., Santajit, S., et al., Mechanisms of Antimicrobial Resistance in ESKAPE Pathogens (2016) Biomed Res Int. 2016; 2016:2475067, doi: 10.1155/2016/2475067).

Typical clinical irrigation solutions include normal saline or lactated ringers. The effect of pH and these buffered solutions on the needed contact time for treatment with antimicrobials was unknown. The objective of this study was to understand the influence of the pH of typical buffer solutions used in the operating room and pH on the antimicrobial activity, and needed contact time of WLBU-2. It was hypothesized that the typical solutions used for irrigation in the operating room, normal saline and lactated ringers, would result in loss of activity based on lower pH as compared to a more physiologic buffered solution.

Materials and Methods

Bacterial strains and culture. *S. aureus* SH1000 was used for in vitro assays and the PJI animal model. SH1000 was inoculated in Tryptic Soy Broth (TSB, Becton Dickinson and Company) overnight at 37° C. with shaking at 250 rpm. Strains were diluted in Mueller Hinton Broth (MHB; Bectin Dickinson and Company) to a final concentration of $0.5 \times 10^6$ CFU/ml using the 0.5 MacFarland Standard (GFS Chemicals) and an Infinite M200 Spectrophotometer (Tecan). WLBU-2 (PLG0206) was supplied by Peptilogics (San Jose, California). All experiments were performed at least in triplicate at three separate times with freshly inoculated cultures.

*S. aureus* biofilm implant in vitro killing assays. Implant material was prepared from 0.6 mm diameter stainless steel Kirschner wire (Synthes) and cut into 6 mm length, autoclaved, and plated in wells along with SH1000 and all clinical strains at $1 \times 10^6$ CFU/ml. After plating, fresh MHB media was exchanged at 24 hours. At 48 hours, wire with mature biofilms were either placed into fresh MHB with either cefazolin or WLBU-2. Biofilms were treated with cefazolin at 0.13, 0.25, 0.5, and 1 mg/ml or WLBU-2 at 62, 125, 250, and 500 µg/ml. Cefazolin treated biofilm were removed 2, 6, and 24 hours after drug addition, WLBU-2 treated biofilm were removed 5 min, 20 min, 60 min, and 2 hours after drug addition. After treatment, Kirschner wires were placed in 1 ml of 1% Tween 20 and sonicated for 10 minutes. Sonicate was serially diluted and plated on TSA II with 5% sheep blood CS100 plates blood agar for colony forming unit (CFU) analysis. For pH analysis, prior to WLBU-2 addition, PBS was adjusted to more acidic pH using hydrochloric acid and more alkaline pH using ammonium hydroxide. Infected implant pieces were tested with WLBU-2 at both 0.5 and 1.0 µg/ml in PBS adjusted to pH of 6.5, 6.8, 7.0, 7.2, 7.4, and 8.0. Biofilm implant pieces were treated at very early time points of 2.5-20 minutes, then CFU analysis was performed.

Periprosthetic Joint Infection Murine Washout Model. Twelve-week-old B57BL/6 J female mice (Jackson) were used for all experiments. Mice were anesthetized by 2% isoflurane, hair was removed from leg and treated with betadine. With a scalpel, a medial parapatellar incision was made, and lateral displacement of the quadriceps-patellar complex allowed for visualization of the femoral intercondylar notch. With a 25-gauge needle, the femoral intramedullary canal was manually reamed. Mature *S. aureus* biofilm previously established on a 0.6 mm wide/6 mm long Kirschner wire (Synthes) was inserted into the reamed canal, and sutured closed. 48 hours later, mice were euthanized and the infected Kirschner wire implant were extracted, placed in WLBU-2 at 1.0 mg/ml in PBS previously pH adjusted to 6.5, 7.0, 7.2, or 7.4 for 10 minutes, and then placed 1% Tween 20 on ice. Implants were sonicated for 10 minutes. Samples were serially diluted and plated on TSA II with 5% sheep blood CS100 plates for CFU analysis.

Statistics

All statistical methods were performed using Prism 7.0 (GraphPad, La Jolla CA). Multiple groups were compared using a Kruskal-Wallis test with a Dunn's Multiple Comparisons posttest. In all cases, $p<0.05$ (*), $p<0.005$ (), $p<0.0005$ (*), and $p<0.0001$ (****) was considered significant.

Results

Figure 2A:
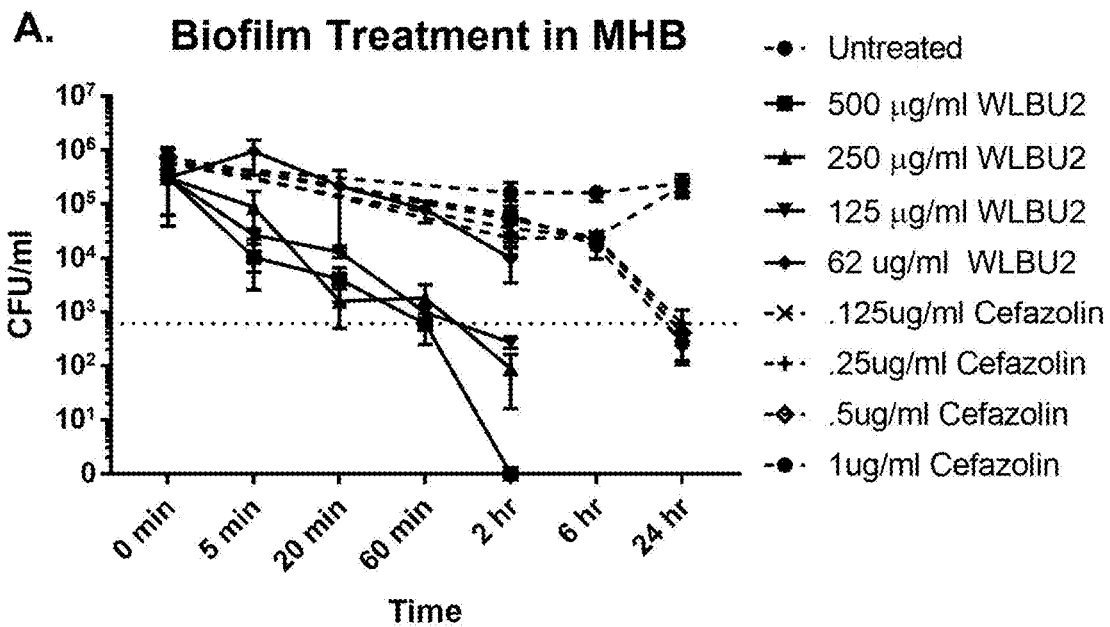
FIGS. 2A and 2B. WLBU-2 displays faster and improved S. aureus biofilm killing in PBS. SH1000 mature biofilms were grown on stainless steel Kirschner wire implant pieces over 48 hours in MHB. Biofilms were washed with PBS and placed into MHB with fold dilutions of WLBU-2 or cefazolin. Biofilm pieces were treated with WLBU-2 for 5-120 minutes, and treated with cefazolin for 2, 6, and 24 hours. Treated biofilms were washed with PBS, placed into 1% Tween 20 in PBS sonication solution and sonicated for 10 minutes. Colony forming unit (CFU) quantification on blood agar plates was performed to determine biofilm burden present after treatment (FIG. 2A). Biofilm implant pieces were treated at very early time points of 5-30 minutes with WLBU-2 in PBS. Biofilms were washed with PBS and processed for CFU analysis. Treatment using WLBU-2 in PBS resulted in increased speed and magnitude of biofilm killing compared to treatment in MHB, red line represents 99.9% decrease in untreated biofilm bacterial burden (FIG. 2B).
Figure 2B:
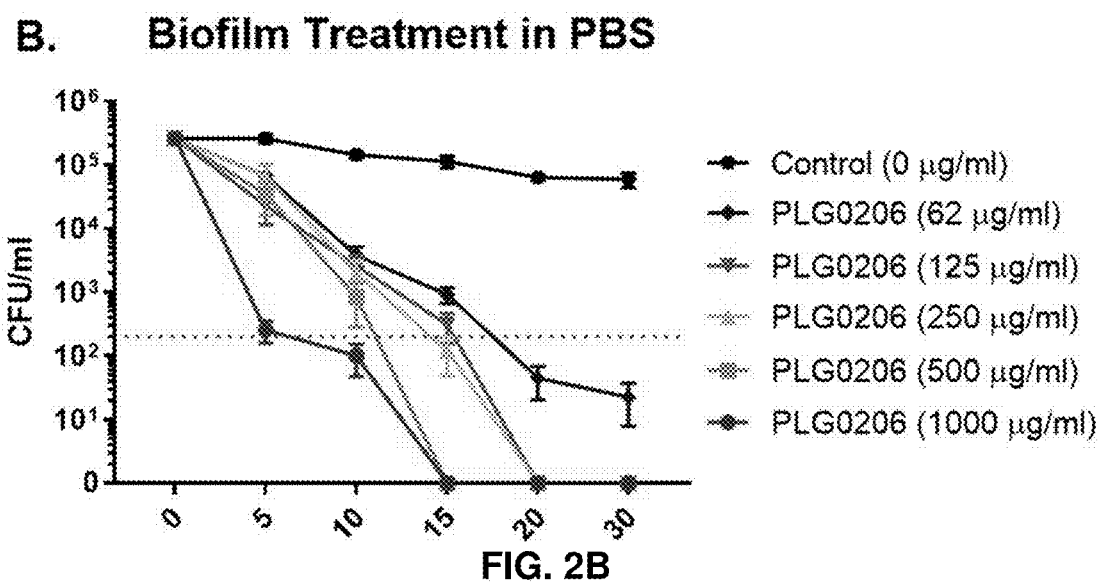

WLBU-2 activity is decreased in typical buffered solutions used in clinic. Activity of WLBU-2 was tested on the common clinically used buffered solutions for irrigation, normal saline and lactated ringers. These results were compared to a physiologic buffered solution, Phosphate Buffered Saline, and MHB media, typical culture media used to measure MIC in microbiology laboratories. Biofilms grown on Kirschner wire implant pieces displayed $0.2\text{-}1.0 \times 10^6$ CFU/ml over 24 hours when left untreated. Cefazolin treatment resulted in only a modest decrease in biofilm CFU over 6 hours, and requires over 24 hours to achieve 99.9% reduction of CFU compared untreated implant pieces (FIG. 2A). In contrast WLBU-2 treatment resulted in faster reduction in biofilm CFU, achieving a 99.9% reduction in under 2 hours when treated in MHB media (FIG. 2A). Treatment of biofilms with WLBU-2 in buffered PBS resulted in increased magnitude and speed of killing with doses of 62-1000 µg/ml all able to achieve a 99.9% reduction dotted lines in biofilm CFU within 20 minutes (FIG. 1B).

Figure 3A:
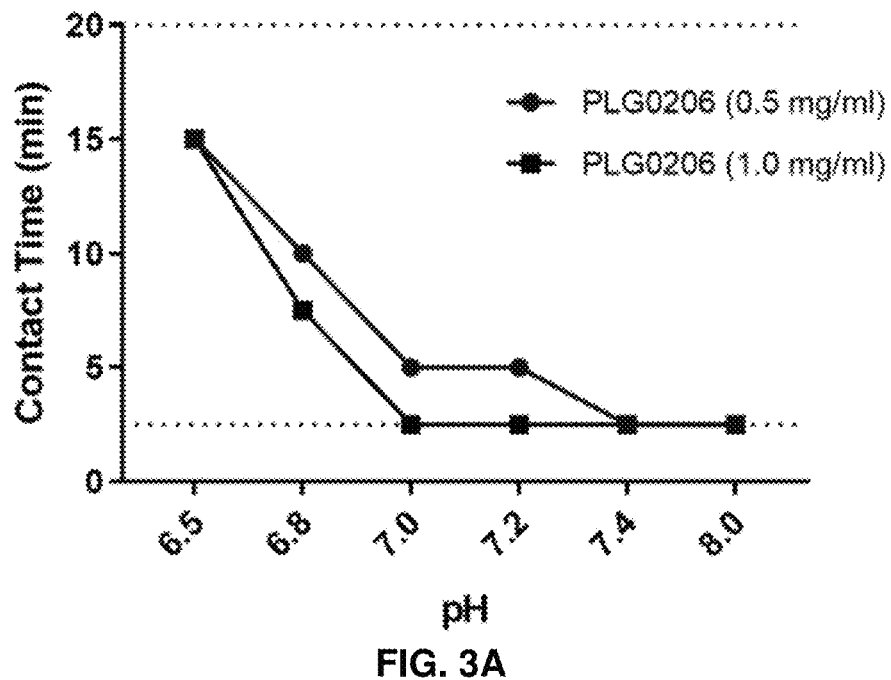
FIGS. 3A and 3B. Alkaline adjusted PBS enhances WLBU-2 activity against S. aureus biofilms. Biofilm implant pieces were treated at early time points of 2.5-20 minutes with WLBU-2 in PBS. PBS pH was adjusted from 6.5 to 8.0 before peptide addition and biofilm treatment. Treated biofilms were placed into 1% Tween 20 in PBS sonication solution and sonicated for 10 minutes. CFU quantification on blood agar plates was performed to determine a three-log reduction from untreated controls. Contact time needed to obtain a three-log reduction in biofilm CFU was reduced with increasing pH (FIG. 3A). Additionally, CFU analysis displayed WLBU-2 treatment with PBS at alkaline values were able to obtain 0 CFU sterile samples after sonication (FIG. 3B).
Figure 3B:
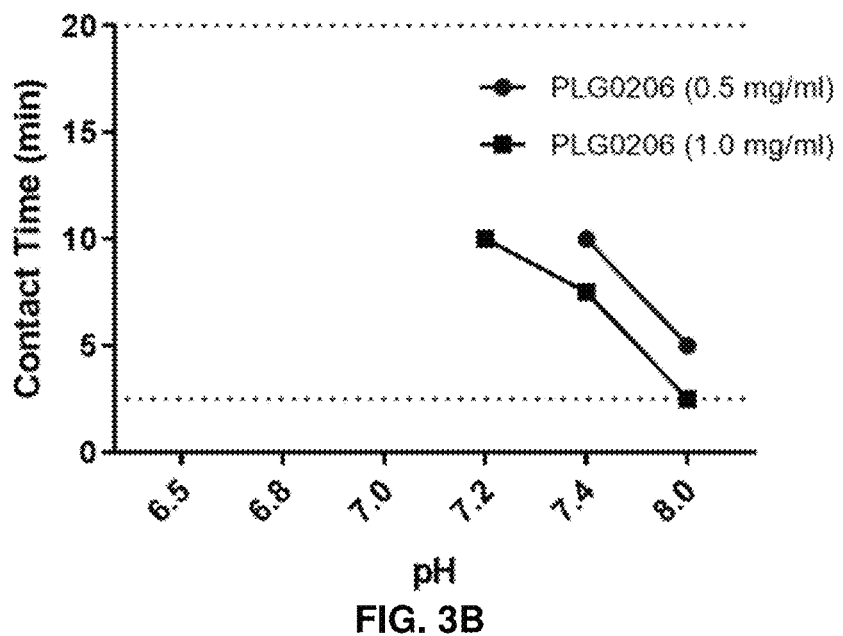

Physiologic pH enhances WLBU-2 activity against *S. aureus* biofilms. After observing large differences in WLBU-2 activity in different buffered solutions, it was questioned if needed contact time for therapeutic treatment would be altered by pH. Mature biofilm was again cultured on surgical implant material and needed contact time of WLBU-2 as a function of pH was determined. PBS pH was adjusted from 6.5 to 8.0 before peptide addition and biofilm treatment. CFU quantification on blood agar plates was performed to determine a three-log reduction from untreated controls (FIG. 3A). A clear reduction in contact time needed to obtain a three-log reduction was observed as the pH was increased to more alkaline conditions. At 1.0 mg/ml WBLU2 in 6.5 pH PBS needed 15 minutes to achieve a three-log reduction while WLBU-2 in 8.0 pH PBS only needed 2.5 minutes (FIG. 3A). Additionally, CFU analysis displayed WLBU-2 treatment with PBS at alkaline values of 7.4 and 8.0 were able to obtain 0 CFU sterile samples (FIG. 3B).

Figure 4:
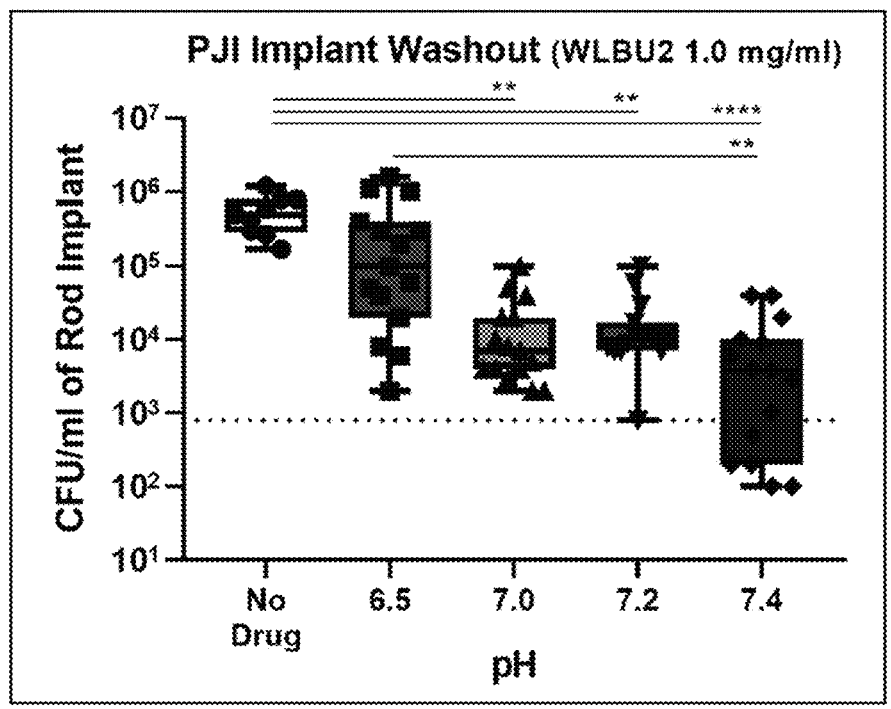
FIG. 4. Alkaline adjusted WLBU-2 washout improves PJI implant biofilm treatment Mature SH1000 biofilms were grown on Kirschner wire implant pieces for 48 hours and inserted into a manually reamed proximal femur before closing with sutures in a murine model of PJI. Two days later, implant pieces were retrieved from mice and placed directly into pH adjusted PBS with WLBU-2 dissolved at 1.0 mg/ml for 10 minutes. Implant pieces were sonicated and plated for CFU analysis to determine implant bacterial burden. PJI implants treated with WLBU-2 in more alkaline PBS pH of 7.0, 7.2, and 7.4 displayed a significant reduction in biofilm CFU compared to untreated control (No Drug). WLBU-2 washout in 7.4 pH PBS displayed significantly less CFU implant burden compared to WLBU-2 washout in 6.5 pH PBS. Black line represents a 99.9% decrease compared to PBS washout only (No Drug).

Alkaline adjusted WLBU-2 washout improves PJI implant biofilm treatment. The dependence of pH and buffered solution on WLBU-2 activity was confirmed in a murine PJI animal model. Mature biofilms grown on Kirschner wire implant pieces were inserted into knee joint space and sutured closed. 48 hours later the implant pieces were obtained and treated with WLBU-2 in pH-adjusted PBS at 1.0 mg/ml for 10 minutes. CFU analysis was performed on infected implant pieces with WLBU-2 washout using pH adjusted PBS at 6.5, 7.0, 7.2, and 7.4 pH as well as implant pieces treated with PBS at 7.0 with no WLBU-2 (No Drug). WLBU-2 washout using pH adjusted to 7.0, 7.2, and 7.4 all displayed significant reduction in biofilm CFU compared to the No Drug group. Additionally, WLBU-2 washout with 7.4 pH displayed significant reduction of biofilm CFU compared to WLBU-2 washout with 6.5 pH (FIG. 4).

In sum, WLBU-2 displays faster and improved S. aureus biofilm killing in PBS compared to more biologically complex MHB. Alkaline-adjusted PBS enhanced WLBU-2 activity against S. aureus biofilms. And alkaline conditions improve WLBU-2 activity against S. aureus biofilm in a PJI washout mouse model. Currently, Betadine, $H_2O_2$, or chlorohexidine suspended in saline or lactated ringers are used as antimicrobial washes. Results presented herein demonstrate that WLBU-2 has potential application to irrigation. Lactated ringers have ~6.5 pH and normal saline can be even more acidic ~5.5 pH. Antimicrobial activity is best when using WLBU-2 in direct contact with biofilms. This works great with using WLBU-2 at relatively high doses locally during and I&D of PJI or any surgical site infection. Data provided herein indicates that local washout using WLBU-2 as an antimicrobial, is best performed in an alkaline solution, such as alkaline-buffered saline, resulting in faster, and more complete biofilm killing and clearance.

Example 2

S. aureus mature biofilms were grown on metal implant material and treated with WLBU-2 dissolved in differing washout solvents. Mature biofilms were treated both in vitro as well as in a periprosthetic joint infection murine model. WLBU-2 activity against S. aureus biofilms was increased when dissolved in dPBS with pH of 7.0 compared to normal saline with pH of 5.5. WLBU-2 activity could be decreased in acidic dPBS and increased in alkaline dPBS. WLBU-2 activity could be decreased in hypertonic dPBS and increased in hypotonic dPBS. WLBU-2 dissolved in less acidic dPBS displayed increased efficacy in treating PJI washout murine model. WLBU-2 displays the ability to sterilize PJI associated S. aureus biofilms on arthroplasty material. The efficacy of engineered cationic amphipathic peptide WLBU-2 for intraoperative sterilization of S. aureus biofilms can be further optimized when kept in a less acidic and more physiologic pH adjusted saline.

The objective of this study was to understand the influence of the pH and ionic strength of typical buffer solutions used in the operating room and pH on the antimicrobial activity and needed contact time of WLBU-2. It was hypothesized that the typical solutions used for irrigation in the operating room, normal saline and lactated ringers, would result in loss of activity based on lower pH as compared to a more physiologic buffered solution. The effects of pH and ionic strength on altering contact time to reduce biofilm burden remain unknown. This would have important formulary implications to minimize needed contact time in direct topical application of this antibiotic as compared to intravenous delivery.

Materials and Methods

Bacterial strains and culture. S. aureus SH1000 was used for in vitro assays and the PJI animal model. SH1000 was inoculated in Tryptic Soy Broth (TSB, Becton Dickinson and Company) overnight at 37° C. with shaking at 250 rpm. Strains were diluted in Mueller Hinton Broth (MHB; Becton Dickinson and Company) to a final concentration of $0.5 \times 10^6$ CFU/ml using the 0.5 MacFarland Standard (GFS Chemicals) and an Infinite M200 Spectrophotometer (Tecan). WLBU-2 (PLG0206) was supplied by Peptilogics (San Jose, California). All experiments were performed at least in triplicate at three separate times with freshly inoculated cultures.

S. aureus biofilm implant in vitro killing assays. Implant material was prepared from 0.6 mm diameter stainless steel Kirschner wire (Synthes) and cut into 6 mm length, autoclaved, and plated in wells along with SH1000 and all clinical strains at $1 \times 10^6$ CFU/ml. After plating, fresh MHB media was exchanged at 24 hours. At 48 hours, wire with mature biofilms were either placed into fresh MHB, normal saline, lactated ringers, or dPBS with fold dilutions of WLBU-2 at 62, 125, 250, 500, and 1000 µg/ml. dPBS solutions were prepared using any combination of the salt buffers listed in Table 3, dissolved in sterile, deionized water. After treatment, Kirschner wires were placed in 1 ml of 1% Tween 20 in dPBS and sonicated for 10 minutes. Sonicate was serially diluted and plated on TSA II with 5% sheep blood CS100 plates blood agar for colony forming unit (CFU) analysis. For pH analysis, prior to WLBU-2 addition, dPBS was adjusted to more acidic pH using hydrochloric acid and more alkaline pH using ammonium hydroxide. Infected implant pieces were tested with WLBU-2 at both 0.5 and 1.0 mg/ml in PBS adjusted to pH of 6.5, 6.8, 7.0, 7.2, 7.4, and 8.0. For ionic strength analysis, dPBS was adjusted to hypertonic conditions by addition of NaCl to dPBS (0.3 M) and hypotonic conditions by addition of deionized water to dPBS (0.08 M). Biofilm implant pieces were treated with WLBU-2 at 0.12, 0.25, 0.5, and 1.0 mg/ml at very early time points of 2.5-20 minutes, then CFU analysis was performed.

TABLE 3

| Salt Buffer and Alternative Salt Buffer Ingredients | Osmolarity (mOsm/L) |
| --- | --- |
| NaCl | 20-200 |
| KCl | 2-50 |
| $KH_2PO_4$ | 2-50 |
| $Na_2HPO_4$ | 2-50 |
| $CaCl_2$ | 2-50 |
| $NaC_3H_5O_3$ | 2-50 |
| $CuCl_2/CuSO_4/C_{11}H_{22}CuO_{14}$ | 2-50 |

Periprosthetic Joint Infection Murine Washout Model. Twelve-week-old B57BL/6 J female mice (Jackson) were used for all experiments. Mice were anesthetized by 2% isoflurane, hair was removed from leg and treated with betadine. With a scalpel, a medial parapatellar incision was made, and lateral displacement of the quadriceps-patellar complex allowed for visualization of the femoral intercondylar notch. With a 25-gauge needle, the femoral intramedullary canal was manually reamed. Mature S. aureus biofilm previously established on a 0.6 mm wide/6 mm long Kirschner wire (Synthes) was inserted into the reamed canal, and sutured closed. 48 hours later, mice were euthanized and the infected Kirschner wire implant were extracted, placed in WLBU-2 at 1.0 mg/ml in PBS previously pH adjusted to 6.5, 7.0, 7.2, or 7.4 for 10 minutes, and then placed 1% Tween 20 on ice. Implants were sonicated for 10 minutes. Samples were serially diluted and plated on TSA II with 5% sheep blood CS100 plates for CFU analysis.

Statistics

All statistical methods were performed using Prism 7.0 (GraphPad, La Jolla CA). Multiple groups were compared using a Kruskal-Wallis test with a Dunn's Multiple Comparisons post-test. In all cases, $p<0.05$ (*), $p<0.005$ (), $p<0.0005$ (*), and $p<0.0001$ (****) was considered significant.

Results

Figure 5:
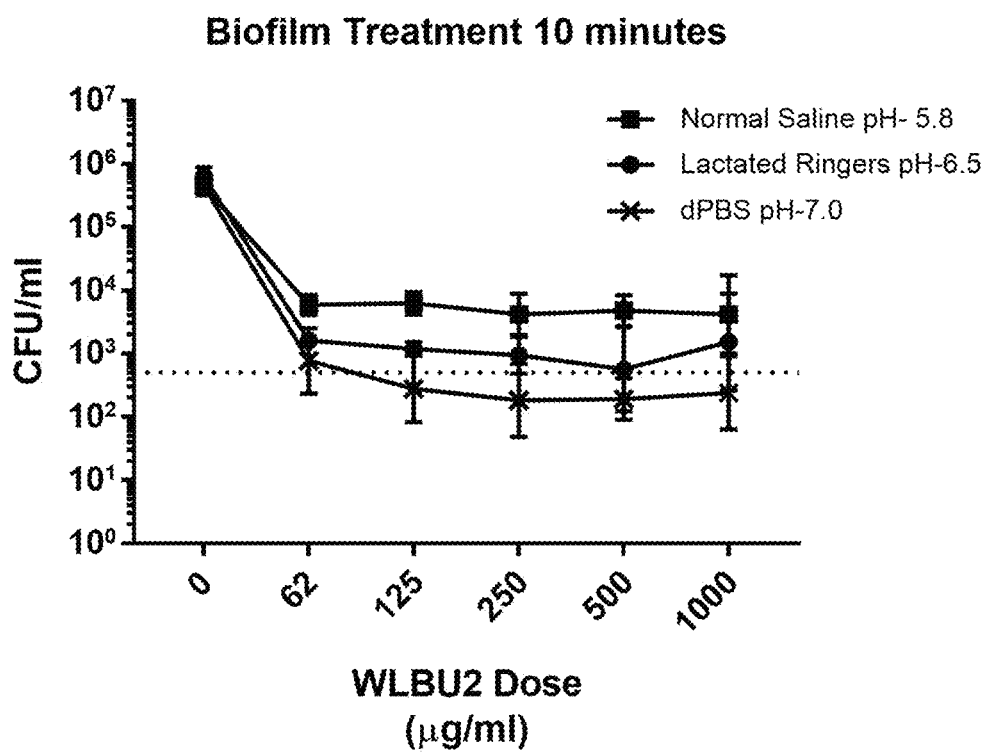
FIG. 5. WLBU-2 displays improved S. aureus biofilm killing in dPBS. SH1000 mature biofilms were grown on stainless steel Kirschner wire implant pieces over 48 hours in MHB. Biofilms were washed with dPBS and placed into MHB with fold dilutions of WLBU-2 or cefazolin. Biofilms were treated with WLBU-2 for 10 minutes, in normal saline, lactated ringers, and dPBS. Treated biofilms were washed with PBS, placed into 1% Tween 20 in dPBS sonication solution and sonicated for 10 minutes. Colony forming unit (CFU) quantification on blood agar plates was performed to determine biofilm burden present after treatment. Black line represents a 99.9% decrease compared to washout only CFU burden.

WLBU-2 activity is decreased in typical buffered solutions used in the clinic. Activity of WLBU-2 was tested in common clinically used buffered solutions for irrigation of a PJI in the operating room, normal saline and lactated ringers as a function of dose. These results were compared to a physiologic Phosphate Buffered Saline a typical culture washing media used in microbiology laboratories. Normal saline with a measured pH of 5.8 displayed nearly 99% reduction in bacterial biofilm CFUs with WLBU-2 at 62-1000 µg/ml. In comparison, Lactated ringers and dPBS with pH of 6.5 and 7.0 respectively displayed over 99.9% reduction in bacterial biofilm with WLBU at 62-1000 µg/ml. WLBU-2 had a higher efficacy at reducing biofilm mass on an implant surface in higher pH solutions that was dose dependent at lower concentration of WLBU-2. As shown in FIG. 5, all three washout solutions have distinct range of pH but also contain differing amounts of buffers which result in slightly different osmolarity and ionic strengths (normal saline—308 mOsm/L, 0.15 M; lactated ringers—274 mOsm/L, 0.14 M; dPBS—299 mOsm/L, 0.16 M).

Figure 6:
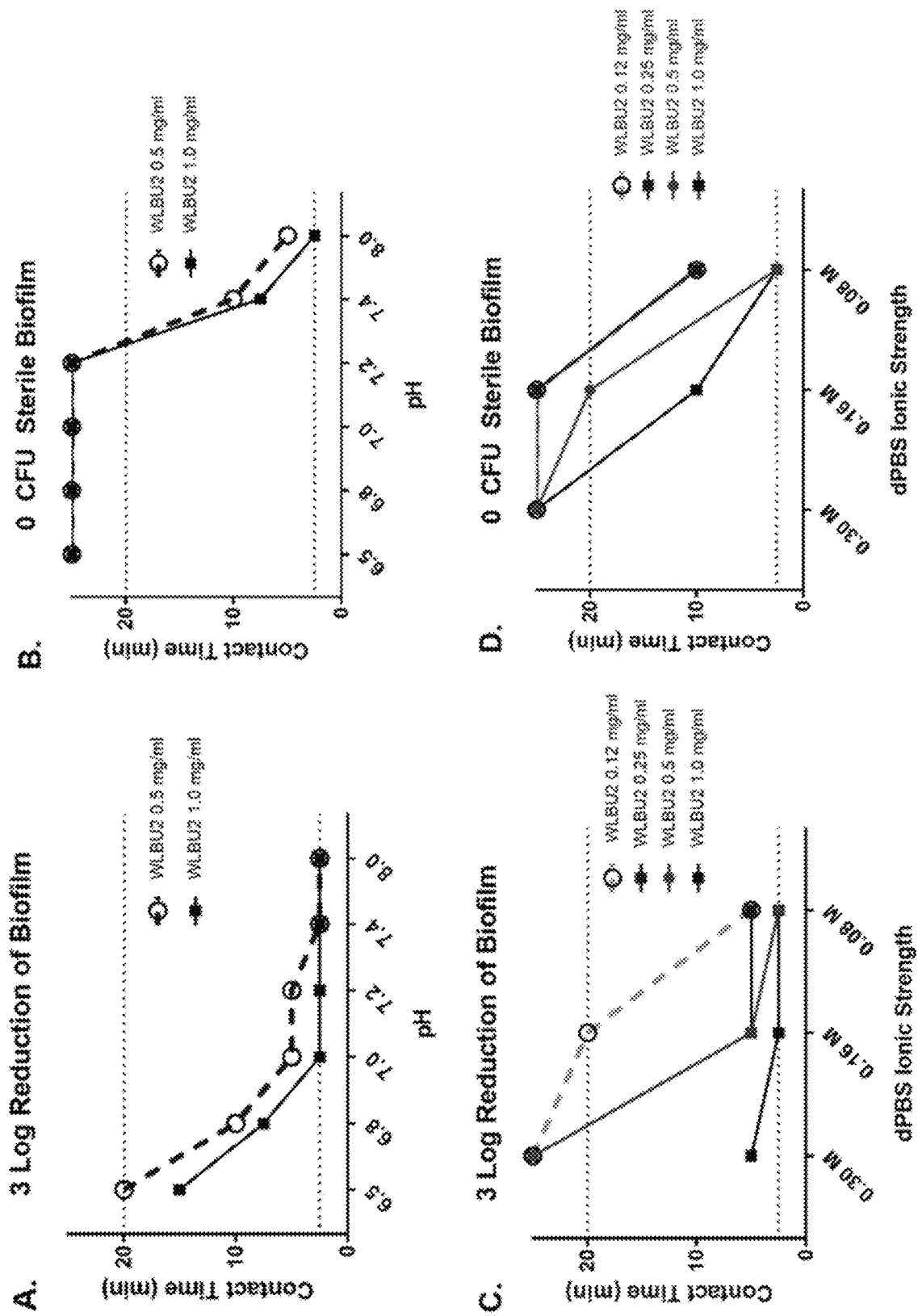
FIG. 6. pH and ionic strength adjusted dPBS enhances WLBU-2 activity against S. aureus biofilms. Biofilm implant pieces were treated at very early time points of 2.5-20 minutes with WLBU-2 in PBS. PBS pH was adjusted from 6.5 to 8.0 before peptide addition and biofilm treatment. Contact time needed to obtain a three-log reduction in biofilm CFU was reduced with increasing pH (A). Additionally, CFU analysis displayed WLBU-2 treatment with PBS at alkaline values were able to obtain 0 CFU sterile samples after sonication (B). Biofilms were similarly treated with WLBU-2 in ionic strength adjusted dPBS and contact time needed for 3 log reduction (C) and 0 CFU sterile (D). Black line displays smallest (2.5 min) and largest (20 min) WLBU-2 contact time recorded values above 20 min were unable to achieve either 3 log reduction or 0 CFU sterile biofilm.

Physiologic pH enhances WLBU-2 activity against S. aureus biofilms. After observing large differences in WLBU-2 activity in different buffered solutions, it was questioned if needed contact time for therapeutic treatment would be altered by pH and ionic strength of washout solution. Mature biofilm was again cultured on surgical implant material and needed contact time of WLBU-2 as a function of pH and ionic strength was determined. CFU quantification on blood agar plates was performed to determine a three-log reduction from untreated controls (FIG. 6 (A)). A clear reduction in contact time needed to obtain a three-log reduction was observed as the pH was increased to more alkaline conditions. At 1.0 mg/ml WLBU-2 in 6.5 pH PBS needed 15 minutes to achieve a three-log reduction while WLBU-2 in 8.0 pH PBS only needed 2.5 minutes (FIG. 6 (A)). Additionally, CFU analysis displayed WLBU-2 treatment with PBS at more physiologic values of 7.4 and 8.0 were able to obtain 0 CFU sterile samples (FIG. 6 (B)).

Ionic strength alters WLBU-2 activity against S. aureus biofilms. After it was observed that the ability of pH to alter the needed contact time to eliminate biofilm, it was questioned if ionic strength had a similar ability to alter contact time needed to eliminate biofilm. There was an inverse, linear relationship between ionic strength and contact time needed to eliminate biofilm. WLBU-2 in hypotonic dPBS of 0.08 M displayed less time needed to obtain a three-log reduction (FIG. 6 (C)) and 0 CFU sterile samples (FIG. 6 (D)) compared to hypertonic dPBS.

Figure 7:
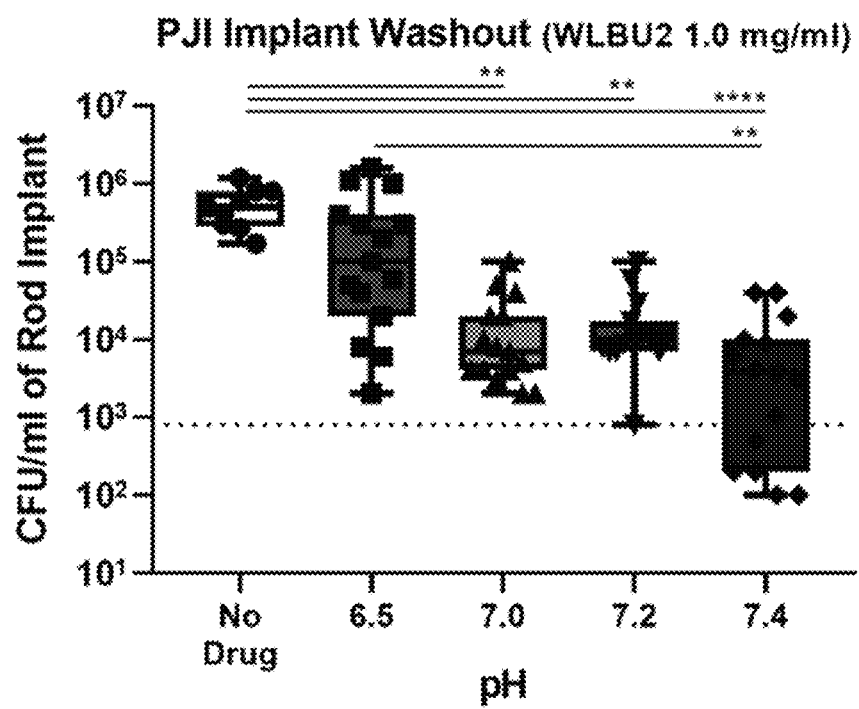
FIG. 7. Physiologic pH adjusted WLBU-2 washout improves PJI implant biofilm treatment. Mature SH1000 biofilms were grown on Kirschner wire implant pieces for 48 hours and inserted into a manually reamed proximal femur before closing with sutures in a murine model of PJI. Two days later, implant pieces were retrieved from mice and placed directly into pH adjusted PBS with WLBU-2 dissolved at 1.0 mg/ml for 10 minutes. Implant pieces were sonicated and plated for CFU analysis to determine implant bacterial burden. PJI implants treated with WLBU-2 in PBS with pH of 7.0, 7.2, and 7.4 displayed a significant reduction in biofilm CFU compared to untreated control (No Drug). WLBU-2 washout in 7.4 pH PBS displayed significantly less CFU implant burden compared to WLBU-2 washout in 6.5 pH PBS. Black line represents a 99.9% decrease compared to PBS washout only (No Drug).

Physiologic pH adjusted WLBU-2 washout improves PJI implant biofilm treatment. The dependence of pH and buffered solution on WLBU-2 activity was confirmed in the murine PJI animal model. Mature biofilms grown on Kirschner wire implant pieces were inserted into knee joint space and sutured closed. 48 hours later the implant pieces were obtained and treated with WLBU-2 in pH adjusted PBS at 1.0 mg/ml for 10 minutes. CFU analysis was performed on infected implant pieces with WLBU-2 washout using pH adjusted PBS at 6.5, 7.0, 7.2, and 7.4 pH as well as implant pieces treated with PBS at 7.0 with no WLBU-2 (No Drug). WLBU-2 washout using pH adjusted to 7.0, 7.2, and 7.4 all displayed significant reduction in biofilm CFU compared to the untreated group. Additionally, WLBU-2 washout with 7.4 pH displayed significant reduction of biofilm CFU compared to WLBU-2 washout with 6.5 pH (See, FIG. 7).

Example 3

Materials and Methods

Bacterial Strains and Culture. SH1000 was inoculated in TSB overnight at 37° C. with shaking at 250 revolutions per minute (rpm). Strains were diluted in MHB to a final concentration of $0.5 \times 10^6$ CFU/mL using the 0.5 MacFarland Standard and an Infinite M200 Spectrophotometer (Tecan). WLBU-2 (PLG0206) was supplied by Peptilogics (San Jose, California).

S. aureus Biofilm Implant in vitro Killing Assays. Implant material was prepared from 0.6 mm diameter stainless steel Kirschner wire (Synthes) and cut into 6 mm length pieces, autoclaved, and plated in wells along with SH1000 and all clinical strains at $1 \times 10^6$ CFU/mL. After plating, fresh MHB media was exchanged at 24 hours. At 48 hours, wires with mature biofilms were either placed into fresh MHB, normal saline, lactated ringers, or dPBS with fold dilutions of WLBU-2 at 62, 125, 250, 500, and 1000 µg/mL. After treatment, the Kirshner wires were placed in 1 mL of 1% Tween 20 in dPBS and sonicated for 10 minutes. The sonicate was serially diluted and plated onto TSA II with 5% sheep blood CS100 plates containing blood agar for CFU analysis. DPBS solutions were adjusted to hypertonic conditions by the addition of NaCl to dPBS and hypotonic conditions by the addition of deionized water to dPBS, and pH adjusted to approximately 7.5 using ammonium hydroxide.

Results

Figure 8:
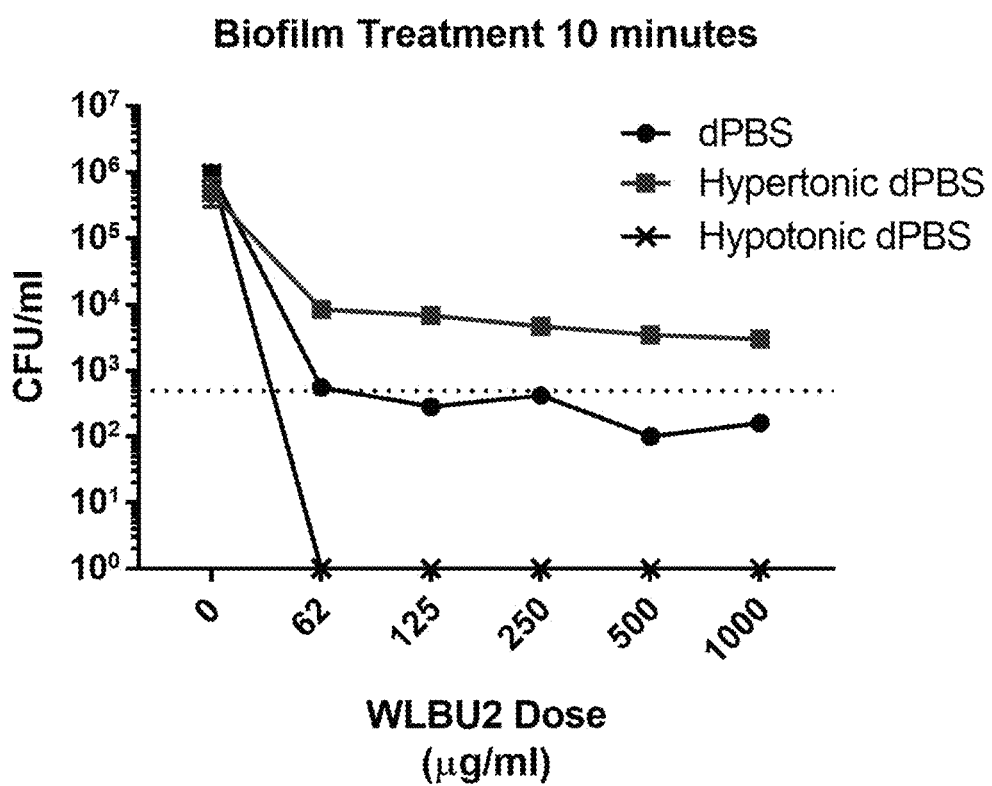
FIG. 8. Physiological pH and ionic strength adjusted dPBS enhances WLBU-2 activity against S. aureus biofilms. Biofilms were treated for 10 minutes with WLBU-2 in dPBS at pH 7.5, hypertonic dPBS at pH 7.5, and hypotonic dPBS at pH 7.5. A three-log reduction in biofilm CFU was achieved with 62, 125, 250, 500, and 1000 µg/mL WLBU-2 in dPBS at pH 7.5 and 0 biofilm CFU was achieved with 62, 125, 250, 500, and 1000 µg/mL WLBU-2 in hypotonic dPBS at pH 7.5. Black line represents a 99.9% decrease compared to dPBS washout only (No Drug).

Physiological pH and ionic strength alter WLBU-2 activity against S. aureus biofilms. The dependence of physiological pH and ionic strength buffered solution on WLBU-2 activity was confirmed. WLBU-2 washout prepared from dPBS at varying ionic strengths and pH 7.5 displayed a reduction in biofilm CFU after 10 minutes of exposure, as compared to the untreated group (FIG. 8). A three-log reduction or greater was achieved for all concentrations of WLBU-2 prepared in dPBS at 7.5, while a three-log reduction was not achieved for WLBU-2 washout prepared in hypertonic dPBS at pH 7.5. WLBU-2 in hypotonic dPBS at pH 7.5 resulted in 0 CFU samples at all concentrations (62, 125, 250, 500, and 1000 µg/mL WBLU2) after 10 minutes of exposure. This study displayed that physiological pH and hypotonic ionic strength adjusted dPBS enhanced WLBU-2 activity against *S. aureus* biofilms.

This study displays that physiologic pH adjusted dPBS enhanced WLBU-2 activity against *S. aureus* biofilms compared to more acidic washout solutions currently used in the operating room like normal saline. Importantly, increasing the pH of the washout solution to above 7.0 resulted in a reduction in contact time needed to obtain above a 99.9% clearance of biofilms to under 5 minutes. Only pH ranges which are applicable in the context of clinically used washout solvents were investigated, not the more acidic and basic extremes.

This work demonstrates that engineered amphipathic peptides, e.g. LLP-1-derived peptides such as WLBU-2, could be utilized to eliminate and significantly reduce *S. aureus* biofilms on arthroplasty material in a short time period which can be achieved in the operating room. More importantly, from a formulation perspective, the pH and ionic strength of the washout solution alters the contact time needed to sterilize or largely eliminate *S. aureus* biofilms. These results demonstrate that WLBU-2 has potential application to treat *S. aureus* biofilms, among other biofilms, during irrigation procedures to reduce biofilm mass or microbe load on arthroplasty material. This is similar to the use of antiseptic solutions such as betadine and chlorohexidine for removing biofilm mass during an implant procedure. Patients who received betadine lavage during surgery have lower chances of developing a deep periprosthetic joint infection. Although betadine is effective, chlorohexidine is also widely used during treatment of PJI. Comparing use of betadine vs chlorohexidine displayed both are effective for treatment of PJI, but neither are superior to each other. The two most commonly used washout solvents are lactated ringers and normal saline which have pH of ~6.5 pH and ~5.5 pH respectively. This would alter the efficacy and contact time needed for WLBU-2 to be efficacious.

A major prior criticism of the use of antimicrobial peptides for treatment of infections was their labile nature. Although lability has been vastly improved upon by the rational design of LLP-1-derived peptides such as WLBU-2, their activity nonetheless has proven best when using WLBU-2 in direct contact with biofilms, and in relatively high doses locally during and I&D of PJI, or washout of any surgical site infection. The data suggests that using WLBU-2 for local washout is better performed in a slightly alkaline and hypotonic buffered saline solution for the best results. The more alkaline and hypotonic the saline solution WLBU-2 is dissolved in will result in faster and better biofilm killing and clearance, with potentially lowering the required concentration of the peptide.

Example 4

Objectives:
The objective of this study is to evaluate the efficacy of WLBU2 in a rabbit periprosthetic joint infection (PJI) model.
Vehicle/Control Article Identification:
Phosphate Buffered Saline pH 7.4 at room temperature
Preparation Details:
Dosing formulations will be prepared in phosphate buffered saline. Measurements for pH (adjusted to 7.4±0.1) and osmolality will be determined for the formulations. A 0.22 uM PVDF will be used to filter each preparation.
Experimental Design:
A PJI New Zealand White Rabbit Animal model was used. A 3D printed tibia titanium implant was placed in the knee, and inoculated with *S. aureus* (strain: SH1000, inoculation density $2\times10^6$) after closure of the arthrotomy.

The rabbit is anesthetized with ketamine 40 mg/kg and xylazine 2 mg/kg during surgery. A bone tunnel in the tibial canal is created using a drill with a 1.2 mm or 1.6 mm tungsten carbide drill bit. The bone tunnel is then dried and treated to simulate acute human PJI following primary arthroplasty. A 3D printed titanium implant will then be placed in the bone tunnel and the wound closed. Prior to closure of the superficial skin layer, 0.1 mL of $2\times10^6$ planktonic bacteria (*S. aureus*; strain: SH1000; CFU/rabbit) in saline is injected into the joint space. A closure is performed, and a biofilm is allowed to become established over 2 days.

After 48 hours, animals were sacrificed and the implants were exposed to either topical cefazolin (10 mg/kg) or topical WLBU2 (1 mg/mL) in PBS (pH 7.4). Implants were sonicated 10 minutes, and colony forming unit (CFU) assay was performed on blood agar plates to quantify bacterial burden.

Figure 9:
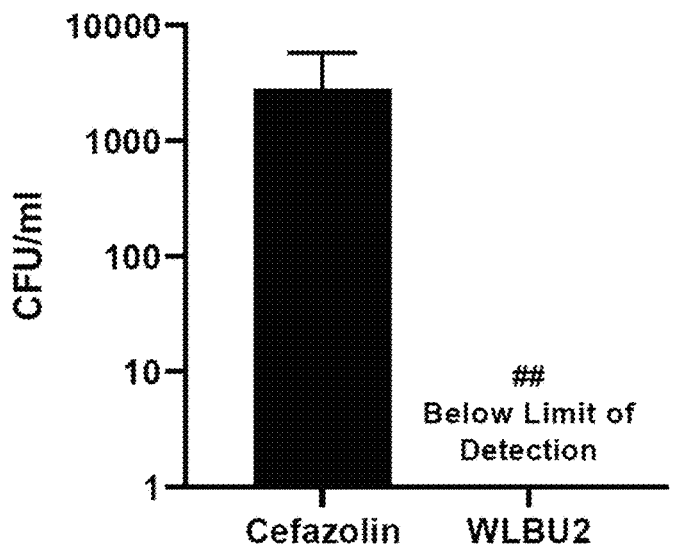
FIG. 9 is a graph depicting initial data obtained for WLBU-2 in a rabbit model, as described in Example 4.

The experiment was completed on three rabbits per group for a total of 6 rabbits. Exclusion criteria included development of an intra-muscular (extra-articular) abscess or perforation of the femoral canal as these two scenarios are not commonly observed with periprosthetic joint infection. Results are shown in FIG. 9 with 3 animals and a total of 9 data points for the cefazolin group and one animal and three data points in the WLBU2 group.

At 2 days post infection irrigation and debridement (I&D) was performed on the infected joint. Treatment with PLG0206 was administered at 1 mg/mL concentration (ex vivo or in vivo) and 0.5 mg/mL concentration (in vivo) at 15 (ex vivo and in vivo), and 7.5 minutes (in vivo) exposure times. For the ex vivo administration, the implant was removed and exposed to PLG0206 solution in a tube for 15 minutes. For the in vivo administration, irrigation and debridement on the joint was performed followed by PLG0206 treatment. The animals were euthanized after treatment, and the implants removed post mortem.

Figure 10:
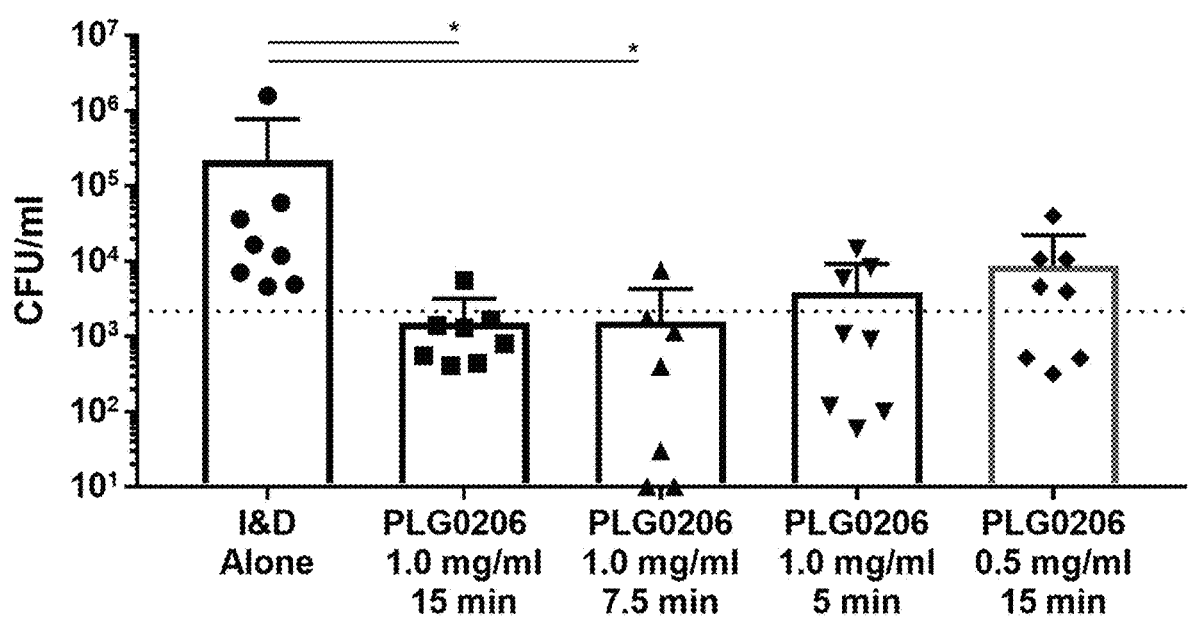
FIG. 10. PLG0206 treated groups were significantly different in comparison control groups for both ex vivo and in vivo treatments with a greater than 2 log reduction in bacterial burden. In the in vivo study, 1 mg/ml PLG0206 for 15 minutes had a significantly greater reduction in bacterial burden in comparison to 0.5 mg/ml PLG0206. A similar reduction in bacterial burden was observed with 1 mg/ml PLG0206 treatment for 7.5 minutes.

PLG0206 treated groups were significantly different in comparison control groups for both ex vivo and in vivo treatments with a greater than 2 log reduction in bacterial burden. In the in vivo study, 1 mg/ml PLG0206 for 15 minutes had a significantly greater reduction in bacterial burden in comparison to 0.5 mg/ml PLG0206. A similar reduction in bacterial burden was observed with 1 mg/ml PLG0206 treatment for 7.5 minutes (FIG. 10).

At 2 days post infection I&D will be performed on the infected joint and treatments will begin. Animals will receive treatment with an I&D alone, I&D with PLG0206, systemic treatment with cefazolin, or both PLG0206 and cefazolin When an animal dies or is sick and needs to be euthanized, the implant and a part of the tibia will be collected post mortem and bacterial burden will be determined by CFU. All surviving animals will be euthanized on Day 28 and the implant and tibia will be collected post mortem for CFU analysis.

Figure 11:
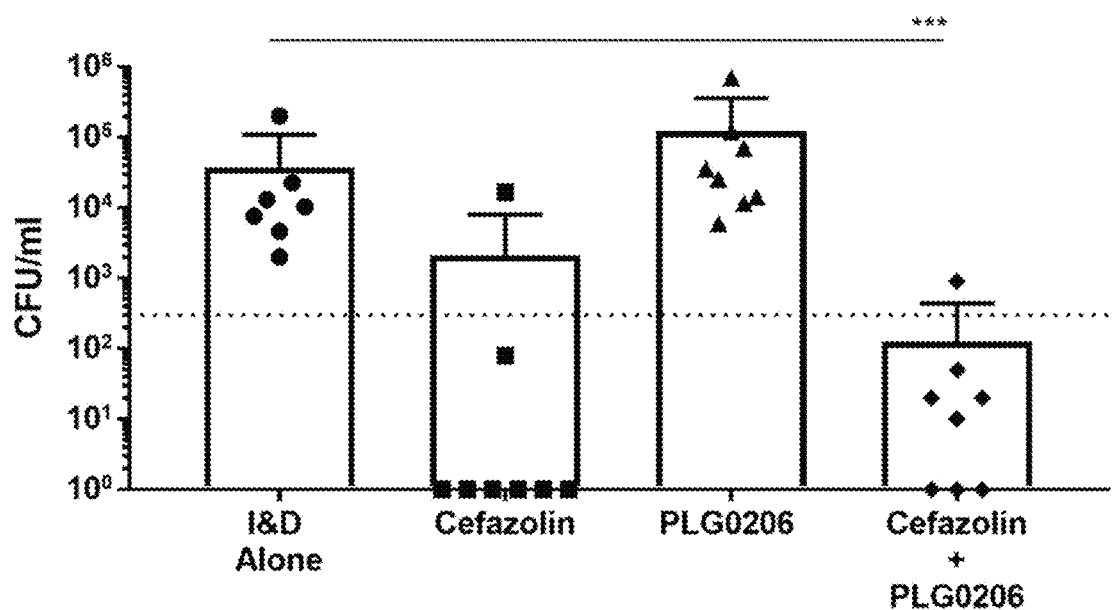
FIG. 11. 1 mg/ml PLG0206 treatment alone (Group 3) was not significant in comparison to control. However, 1 mg/ml PLG0206 treatment in combination with cefazolin (Group 4) resulted in a significant reduction (2.5 log) in bacterial burden (FIG. 11). Cefazolin treatment alone (Group 2) was not sufficient to eliminate the biofilm with only a 1.5 log reduction in bacterial burden.

1 mg/ml PLG0206 treatment alone (Group 3) was not significant in comparison to control. However, 1 mg/ml PLG0206 treatment in combination with cefazolin (Group 4) resulted in a significant reduction (2.5 log) in bacterial burden (FIG. 11). Cefazolin treatment alone (Group 2) was not sufficient to eliminate the biofilm with only a 1.5 log reduction in bacterial burden.

Having described this invention, it will be understood to those of ordinary skill in the art that the same can be performed within a wide and equivalent range of conditions, formulations, and other parameters without affecting the scope of the invention or any embodiment thereof.

The invention claimed is:

1. A method of treating or preventing an infection in a subject in need thereof, comprising administering a pharmaceutical composition to an open wound, an implant, a medical device, a prosthetic, or any part thereof of the subject, wherein the infection comprises a biofilm, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10; and
   b. a pharmaceutically acceptable aqueous carrier;
   wherein the pharmaceutical composition is in the form of a liquid; wherein the cationic antimicrobial peptide is present at a concentration of about 3 mg/mL to about 30 mg/mL, and wherein the pharmaceutical composition has a total osmolarity from about 50 mOsm/L to about 350 mOsm/L.

2. The method of claim 1, wherein the pharmaceutical composition further comprises a salt that is selected from the group consisting of sodium chloride, potassium chloride, potassium dihydrogen phosphate, disodium phosphate, calcium chloride, sodium lactate, copper chloride, copper sulfate, $C_{11}H_{22}CuO_{14}$, ammonium hydroxide, magnesium hydroxide, sodium carbonate, and any combination thereof.

3. The method of claim 1, wherein the pharmaceutical composition further has a pH of from about 7.2 to about 8.0.

4. The method of claim 1, wherein the administering comprises irrigating the open wound, the implant, the medical device, the prosthetic, or any part thereof using the pharmaceutical composition.

5. The method of claim 4, wherein the irrigating further comprises reducing microbe load, wherein the microbe load is reduced by at least 1000-fold when the irrigating lasts for at most about 30 minutes.

6. The method of claim 1, wherein the treating or preventing the infection further comprises administering an antibiotic to the subject in need thereof.

7. The method of claim 1, wherein the aqueous carrier comprises water, normal saline, phosphate buffered saline, dextrose, glycerol, ethanol, buffered salt solutions, lactated Ringer's solution, or any combination thereof.

8. The method of claim 1, wherein the pharmaceutical composition further has a pH of from about 5.0 to about 8.0.

9. The method of claim 1, wherein the pharmaceutical composition further has a pH from about 7.4 to about 8.0.

10. The method of claim 1, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

11. The method of claim 1, wherein the infection comprises periprosthetic joint infection.

12. The method of claim 1, wherein the method is subsequent to an irrigation and debridement (I&D) of the open wound, the implant, the medical device, the prosthetic, or any part thereof, wherein said I&D comprises use of a betadine, a chlorohexidine, or saline solution.

13. The method of claim 1, further comprising administering an antibiotic selected from the group consisting of: Aminoglycoside, Carbapenem, Ceftazidime, Cefepime, Ceftobiprole, Ceftaroline, Clindamycin, Cefazolin, Dalbavancin, Daptomycin, Fluoroquinolone, Linezolid, Mupirocin, Oritavancin, Piperacillin, Silver nitrate, Streptogramin, Telavancin, Tedizolid, Ticarcillin, Tigecycline, Vancomycin, and any combination thereof.

14. The method of claim 1, wherein the method reduces a bacterial burden of the biofilm by at least $10^2$ CFU/mL as determined by a CFU quantification assay compared to an untreated subject.

15. The method of claim 1, wherein the method reduces a bacterial burden of the biofilm by at least a three-log reduction as determined by a CFU quantification assay compared to an untreated subject.

16. The method of claim 1, wherein the method reduces a bacterial burden of the biofilm by 99.9%.

17. A method of treating or preventing an infection in a subject in need thereof, comprising irrigating an open wound, an implant, a medical device, a prosthetic, or any part thereof of the subject using a pharmaceutical composition, wherein the infection comprises a biofilm, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10, and wherein the cationic antimicrobial peptide is present at a concentration of about 3 mg/mL to about 30 mg/mL; and b. a pharmaceutically acceptable aqueous carrier;
wherein the pharmaceutical composition is in the form of a liquid; and wherein the irrigating is performed at least once a day.

18. The method of claim 17, wherein the cationic antimicrobial peptide is present at a concentration of about 10 mg/mL.

19. The method of claim 17, wherein the aqueous carrier comprises water, normal saline, phosphate buffered saline, dextrose, glycerol, ethanol, buffered salt solutions, lactated Ringer's solution, or any combination thereof.

20. The method of claim 17, wherein the pharmaceutical composition further has a pH of from about 5.0 to about 8.0.

21. The method of claim 17, wherein the pharmaceutical composition further has a pH from about 7.2 to about 8.0.

22. The method of claim 17, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

23. The method of claim 17, wherein the infection comprises periprosthetic joint infection.

24. The method of claim 17, wherein the method is subsequent to an irrigation and debridement (I&D) of the open wound, the implant, the medical device, the prosthetic, or any part thereof, wherein said I&D comprises use of a betadine, a chlorohexidine, or saline solution.

25. A method of treating or preventing an infection in a subject in need thereof, comprising irrigating an open wound, an implant, a medical device, a prosthetic, or any part thereof of the subject using a pharmaceutical composition, wherein the infection comprises a biofilm, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10, and wherein the cationic antimicrobial peptide is present at a concentration of about 3 mg/mL to about 30 mg/mL; and
   b. a pharmaceutically acceptable aqueous carrier;
   wherein the pharmaceutical composition is in the form of a liquid; and wherein the irrigating using the pharmaceutical composition is performed for a period ranging from about 0.1 min to about 30 min.

26. The method of claim 25, wherein the irrigating using the pharmaceutical composition is performed for a period of about 15 min.

27. The method of claim 25, wherein the cationic antimicrobial peptide is present at a concentration of about 10 mg/mL.

28. The method of claim 25, wherein the aqueous carrier comprises water, normal saline, phosphate buffered saline, dextrose, glycerol, ethanol, buffered salt solutions, lactated Ringer's solution, or any combination thereof.

29. The method of claim 25, wherein the pharmaceutical composition further has a pH of from about 5.0 to about 8.0.

30. The method of claim 25, wherein the pharmaceutical composition further has a pH from about 7.2 to about 8.0.

31. The method of claim 25, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

32. The method of claim 25, wherein the infection comprises periprosthetic joint infection.

33. The method of claim 25, wherein the method is subsequent to an irrigation and debridement (I&D) of the open wound, the implant, the medical device, the prosthetic, or any part thereof, wherein said I&D comprises use of a betadine, a chlorohexidine, or saline solution.

34. A method of treating or preventing an infection in a subject in need thereof, comprising administering a pharmaceutical composition to an open wound, an implant, a medical device, a prosthetic, or any part thereof of the subject, wherein the infection comprises a biofilm, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10, and wherein the cationic antimicrobial peptide is present at a concentration of about 3 mg/mL to about 30 mg/mL; and
   b. a pharmaceutically acceptable aqueous carrier;
   wherein the pharmaceutical composition is in the form of a liquid, and wherein the pharmaceutical composition is physiologically isotonic or physiologically hypotonic.

35. The method of claim 34, wherein the pharmaceutical composition is physiologically isotonic.

36. The method of claim 34, wherein the pharmaceutical composition is physiologically hypotonic.

37. The method of claim 34, wherein the aqueous carrier comprises water, normal saline, phosphate buffered saline, dextrose, glycerol, ethanol, buffered salt solutions, lactated Ringer's solution, or any combination thereof.

38. The method of claim 34, wherein the cationic antimicrobial peptide is present at a concentration of about 10 mg/mL.

39. The method of claim 34, wherein the pharmaceutical composition further has a pH of from about 5.0 to about 8.0.

40. The method of claim 34, wherein the pharmaceutical composition further has a pH from about 7.2 to about 8.0.

41. The method of claim 34, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

42. The method of claim 34, wherein the infection comprises periprosthetic joint infection.

43. The method of claim 34, wherein the method is subsequent to an irrigation and debridement (I&D) of the open wound, the implant, the medical device, the prosthetic, or any part thereof, wherein said I&D comprises use of a betadine, a chlorohexidine, or saline solution.

44. A method of treating or preventing an infection in a subject in need thereof, comprising administering a pharmaceutical composition to an open wound, an implant, a medical device, a prosthetic, or any part thereof of the subject, wherein the infection comprises a biofilm, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10, and wherein the cationic antimicrobial peptide is present at a concentration of about 3 mg/mL to about 30 mg/mL; and
   b. a pharmaceutically acceptable aqueous carrier;
   wherein the pharmaceutical composition is in the form of a liquid; and wherein the pharmaceutical composition comprises a total ionic strength from about 0.02 M to about 0.2 M.

45. The method of claim 44, wherein the cationic antimicrobial peptide is present at a concentration of about 10 mg/mL.

46. The method of claim 44, wherein the aqueous carrier comprises water, normal saline, phosphate buffered saline, dextrose, glycerol, ethanol, buffered salt solutions, lactated Ringer's solution, or any combination thereof.

47. The method of claim 44, wherein the pharmaceutical composition further has a pH of from about 5.0 to about 8.0.

48. The method of claim 44, wherein the pharmaceutical composition further has a pH from about 7.2 to about 8.0.

49. The method of claim 44, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

50. The method of claim 44, wherein the infection comprises periprosthetic joint infection.

51. The method of claim 44, wherein the method is subsequent to an irrigation and debridement (I&D) of the open wound, the implant, the medical device, the prosthetic, or any part thereof, wherein said I&D comprises use of a betadine, a chlorohexidine, or saline solution.

52. A method of treating or preventing an infection in a subject in need thereof, comprising administering a pharmaceutical composition to an open wound, an implant, a medical device, a prosthetic, or any part thereof of the subject, wherein the infection comprises a biofilm, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10, and wherein the cationic antimicrobial peptide is present at a concentration of about 10 mg/mL; and
   b. a pharmaceutically acceptable aqueous carrier;
   wherein the pharmaceutical composition is in the form of a liquid.

53. The method of claim 52, wherein the aqueous carrier comprises water, normal saline, phosphate buffered saline, dextrose, glycerol, ethanol, buffered salt solutions, lactated Ringer's solution, or any combination thereof.

54. The method of claim 52, wherein the pharmaceutical composition further has a pH of from about 5.0 to about 8.0.

55. The method of claim 52, wherein the pharmaceutical composition further has a pH from about 7.2 to about 8.0.

56. The method of claim 52, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

57. The method of claim 52, wherein the infection comprises periprosthetic joint infection.

58. The method of claim 52, wherein the method is subsequent to an irrigation and debridement (I&D) of the open wound, the implant, the medical device, the prosthetic, or any part thereof, wherein said I&D comprises use of a betadine, a chlorohexidine, or saline solution.

59. A method of treating or preventing an infection in a subject in need thereof, comprising injecting a pharmaceutical composition to an open wound, an implant, a medical device, a prosthetic, or any part thereof of the subject, thereby treating or preventing the infection, wherein the pharmaceutical composition comprises:
   a. a cationic antimicrobial peptide or pharmaceutically acceptable salt thereof, wherein the cationic antimicrobial peptide is SEQ ID NO: 10, and wherein the cationic antimicrobial peptide is present at a concentration of about 3 mg/mL to about 30 mg/mL; and
   b. a pharmaceutically acceptable aqueous carrier;
   wherein the pharmaceutical composition is in the form of a liquid.

60. The method of claim 59, wherein the cationic antimicrobial peptide is present at a concentration of about 10 mg/mL.

61. The method of claim 59, wherein the aqueous carrier comprises water, normal saline, phosphate buffered saline, dextrose, glycerol, ethanol, buffered salt solutions, lactated Ringer's solution, or any combination thereof.

62. The method of claim 59, wherein the pharmaceutical composition further has a pH of from about 5.0 to about 8.0.

63. The method of claim 59, wherein the pharmaceutical composition further has a pH from about 7.2 to about 8.0.

64. The method of claim 59, wherein the infection comprises a bacteria species comprising *Enterococcus faecium, Staphylococcus aureus, Klebsiella pneumoniae, Acinetobacter baumannii, Pseudomonas aeruginosa, Enterobacter species, Escherichia coli*, or any combination thereof.

65. The method of claim 59, wherein the infection comprises periprosthetic joint infection.

66. The method of claim 59, wherein the method is subsequent to an irrigation and debridement (I&D) of the open wound, the implant, the medical device, the prosthetic, or any part thereof, wherein said I&D comprises use of a betadine, a chlorohexidine, or saline solution.

\* \* \* \* \*

SEQUENCE LISTING

<160> NUMBER OF SEQ ID NOS: 16

<210> SEQ ID NO 1
<211> LENGTH: 28
<212> TYPE: PRT
<213> ORGANISM: Artificial Sequence
<220> FEATURE:
<223> OTHER INFORMATION: Antimicrobial peptide SA-5

<400> SEQUENCE: 1

Arg Val Ile Arg Val Val Gln Arg Ala Cys Arg Ala Ile Arg His Ile
1               5                   10                  15

Val Arg Arg Ile Arg Gln Gly Leu Arg Arg Ile Leu
            20                  25

<210> SEQ ID NO 2
<211> LENGTH: 31
<212> TYPE: PRT
<213> ORGANISM: Artificial Sequence
<220> FEATURE:
<223> OTHER INFORMATION: Antimicrobial peptide LSA-5

<400> SEQUENCE: 2

Arg Val Ile Arg Val Val Gln Arg Ala Cys Arg Ala Ile Arg His Ile
1               5                   10                  15

Val Arg Arg Ile Arg Gln Gly Leu Arg Arg Ile Leu Arg Val Val
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Antimicrobial peptide WLSA-5

<400> SEQUENCE: 3

Arg Trp Ile Arg Val Val Gln Arg Trp Cys Arg Ala Ile Arg His Ile
1               5                   10                  15

Trp Arg Arg Ile Arg Gln Gly Leu Arg Arg Trp Leu Arg Val Val
            20                  25                  30

<210> SEQ ID NO 4
<211> LENGTH: 12
<212> TYPE: PRT
<213> ORGANISM: Artificial Sequence
<220> FEATURE:
<223> OTHER INFORMATION: Antimicrobial peptide LBU-1

<400> SEQUENCE: 4

Arg Val Val Arg Val Val Arg Arg Val Val Arg Arg
1               5                   10

<210> SEQ ID NO 5
<211> LENGTH: 24
<212> TYPE: PRT
<213> ORGANISM: Artificial Sequence
<220> FEATURE:
<223> OTHER INFORMATION: Antimicrobial peptide LBU-2

<400> SEQUENCE: 5

Arg Arg Val Val Arg Arg Val Arg Arg Val Val Arg Arg Val Val Arg
1               5                   10                  15

Val Val Arg Arg Val Val Arg Arg
            20

<210> SEQ ID NO 6
<211> LENGTH: 35
<212> TYPE: PRT
<213> ORGANISM: Artificial Sequence
<220> FEATURE:
<223> OTHER INFORMATION: Antimicrobial peptide LBU-3

<400> SEQUENCE: 6

Val Arg Val Val Arg Arg Val Val Arg Val Val Arg Arg Val Arg
1               5                   10                  15

Arg Val Arg Arg Val Val Arg Arg Val Val Arg Val Val Arg Arg Val
            20                  25                  30

Val Arg Arg
        35

<210> SEQ ID NO 7
<211> LENGTH: 42
<212> TYPE: PRT
<213> ORGANISM: Artificial Sequence
<220> FEATURE:
<223> OTHER INFORMATION: Antimicrobial peptide LBU-3.5

<400> SEQUENCE: 7

Arg Arg Val Val Arg Arg Val Val Arg Val Val Arg Arg Val Val Arg
1               5                   10                  15

Val Val Arg Arg Val Val Arg Arg Val Arg Arg Val Val Arg Arg Val
            20                  25                  30

Val Arg Val Val Arg Arg Val Val Arg Arg
        35                  40

<210> SEQ ID NO 8
<211> LENGTH: 48
<212> TYPE: PRT
<213> ORGANISM: Artificial Sequence
<220> FEATURE:
<223> OTHER INFORMATION: Antimicrobial peptide LBU-4

<400> SEQUENCE: 8

Arg Val Val Arg Val Val Arg Arg Val Val Arg Val Val Arg Arg Val
1               5                   10                  15

Val Arg Arg Val Val Arg Val Val Arg Arg Val Val Arg Arg Val Arg
            20                  25                  30

Arg Val Val Arg Arg Val Val Arg Arg Val Val Arg Arg Val Arg Arg
        35                  40                  45

<210> SEQ ID NO 9
<211> LENGTH: 12
<212> TYPE: PRT
<213> ORGANISM: Artificial Sequence
<220> FEATURE:
<223> OTHER INFORMATION: Antimicrobial peptide WLBU-1

<400> SEQUENCE: 9

Arg Val Val Arg Val Val Arg Arg Trp Val Arg Arg
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Antimicrobial peptide WLBU-2

<400> SEQUENCE: 10

```
Arg Arg Trp Val Arg Val Arg Arg Val Trp Arg Val Arg
1               5               10              15

Val Val Arg Arg Trp Val Arg Arg
            20
```

<210> SEQ ID NO 11
<211> LENGTH: 36
<212> TYPE: PRT
<213> ORGANISM: Artificial Sequence
<220> FEATURE:
<223> OTHER INFORMATION: Antimicrobial peptide WLBU-3

<400> SEQUENCE: 11

```
Val Arg Arg Val Trp Arg Arg Val Arg Val Val Arg Arg Trp Val
1               5               10              15

Arg Arg Val Arg Arg Val Trp Arg Arg Val Val Arg Val Val Arg Arg
                20              25              30

Trp Val Arg Arg
            35
```

<210> SEQ ID NO 12
<211> LENGTH: 48
<212> TYPE: PRT
<213> ORGANISM: Artificial Sequence
<220> FEATURE:
<223> OTHER INFORMATION: Antimicrobial peptide WLBU-4

<400> SEQUENCE: 12

```
Arg Val Val Arg Val Val Arg Arg Trp Val Arg Val Arg Arg Val
1               5               10              15

Trp Arg Arg Val Val Arg Val Val Arg Arg Trp Val Arg Arg Val Arg
                20              25              30

Arg Val Trp Arg Arg Val Val Arg Val Val Arg Arg Trp Arg Val Val
            35              40              45
```

<210> SEQ ID NO 13
<211> LENGTH: 6
<212> TYPE: PRT
<213> ORGANISM: Artificial Sequence
<220> FEATURE:
<223> OTHER INFORMATION: Antimicrobial peptide WR6

<400> SEQUENCE: 13

```
Arg Arg Trp Trp Arg Arg
1               5
```

<210> SEQ ID NO 14
<211> LENGTH: 12
<212> TYPE: PRT
<213> ORGANISM: Artificial Sequence
<220> FEATURE:
<223> OTHER INFORMATION: Antimicrobial peptide WR12

<400> SEQUENCE: 14

```
Arg Trp Trp Arg Trp Trp Arg Arg Trp Trp Arg Arg
1               5               10
```

<210> SEQ ID NO 15
<211> LENGTH: 18
<212> TYPE: PRT
<213> ORGANISM: Artificial Sequence
<220> FEATURE:
<223> OTHER INFORMATION: Antimicrobial peptide WR18

```
<400> SEQUENCE: 15

Trp Arg Arg Trp Trp Arg Arg Trp Trp Arg Trp Trp Arg Arg Trp Trp
1               5                   10                  15

Arg Arg

<210> SEQ ID NO 16
<211> LENGTH: 24
<212> TYPE: PRT
<213> ORGANISM: Artificial Sequence
<220> FEATURE:
<223> OTHER INFORMATION: Antimicrobial peptide WR24

<400> SEQUENCE: 16

Arg Arg Trp Trp Arg Arg Trp Arg Arg Trp Trp Arg Arg Trp Trp Arg
1               5                   10                  15

Trp Trp Arg Arg Trp Trp Arg Arg
                20
```